US007732139B2

(12) United States Patent
Choi et al.

(10) Patent No.: US 7,732,139 B2
(45) Date of Patent: Jun. 8, 2010

(54) MULTIPLE SNP FOR DIAGNOSING CARDIOVASCULAR DISEASE, MICROARRAY AND KIT COMPRISING THE SAME, AND METHOD OF DIAGNOSING CARDIOVASCULAR DISEASE USING THE SAME

(75) Inventors: Seung-Hak Choi, Seongnam-si (KR); Yun-sun Nam, Seongnam-si (KR); Jae-Heup Kim, Hwaseong-si (KR); Kyung-Hee Park, Seoul (KR); Yeon-Su Lee, Goyang-si (KR); Hyo-jeong Jeon, Anyang-si (KR); Ok-ryul Song, Seoul (KR); Tae-jin Ahn, Seoul (KR); Kyu-sang Lee, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/435,662

(22) Filed: May 17, 2006

(65) Prior Publication Data

US 2006/0263815 A1    Nov. 23, 2006

(30) Foreign Application Priority Data

May 18, 2005  (KR) ............... 10-2005-0041653
Feb. 24, 2006  (KR) ............... 10-2006-0018449

(51) Int. Cl.
| C12Q 1/68 | (2006.01) |
| C07H 21/02 | (2006.01) |
| C07H 21/04 | (2006.01) |
| C12M 1/36 | (2006.01) |
| C12P 19/34 | (2006.01) |

(52) U.S. Cl. .............. 435/6; 435/287.2; 536/23.1; 536/24.3

(58) Field of Classification Search .............. None
See application file for complete search history.

(56) References Cited

U.S. PATENT DOCUMENTS

| 6,812,339 B1 * | 11/2004 | Venter et al. .............. 536/24.31 |
| 7,300,788 B2 * | 11/2007 | Matsuzaki et al. ....... 435/287.2 |
| 2001/0053519 A1 * | 12/2001 | Fodor et al. .................... 435/6 |
| 2003/0186296 A1 * | 10/2003 | Fodor et al. .................... 435/6 |
| 2005/0063981 A1 * | 3/2005 | Jager et al. .............. 424/185.1 |

FOREIGN PATENT DOCUMENTS

| EP | 1298220 | 4/2003 |
| EP | 1327639 A1 | 7/2003 |
| WO | 9845477 A | 10/1998 |

OTHER PUBLICATIONS

Hirschhorn et al. Genetics in Medicine. vol. 4, No. 2, pp. 45-61, Mar. 2002.*
Ioannidis. Nature Genetics, vol. 29, pp. 306-309, Nov. 2001.*
Fornage, et al. Circulation. May 12, 1998;97(18):1773-9.*
dbSNP build history.*
Haluschka, Marc K. et al.; "Patterns of single-nucleotide polymorphism in candidate genes for blood-pressure homeostasis"; Nature Genetics; Jul. 1999; vol. 22(3), pp. 239-247.
Haga H., et al.; "Gene-based SNP discovery as part of the Japanese Millennium Genome Project: identification of 190562 genetic variations in the human genome";Journal of Human Genetics; vol. 47(11), pp. 605-610; Nov. 2002.
NCBI Single Nucleotide Polymorphism, RefSNP ID: rs251692, NCBI Assay ID: ss24575834 (Aug. 21, 2004).
NCBI Single Nucleotide Polymorphism, RefSNP ID: rs20568, NCBI Assay ID: ss23231 (Dec. 21, 1999).
Written Opinion of the International Searching Authority for Application No. PCT/KR2006/001829 dated Aug. 28, 2006.
International Search Report for Application No. PCT/KR2006/001829 dated Aug. 28, 2006 (All references cited in Search Report are listed above).
Korean Office Action dated Jan. 26, 2007 for Application No. 10-2006-0018449 (All references cited in Office Action cited in IDS submitted Dec. 7, 2006).
Guatelli, John C. et al. "Isothermal, in vitro amplification of nucleic acids by a multienzyme reaction modeled after retroviral replication," Proc. Natl. Acad. Sci. USA (1990) 87: 1874-1878.
Gusella, J.F., "DNA Polymorphism and Human Disease," Ann. Rev. Biochem. (1986) 55: 831-854.
Kwoh, D. Y. et al., "Transcription-based amplification system and detection of amplified human immunodeficiency virus type 1 with a bead-based sandwich hybridization format." Proc. Natl. Acad. Sci. USA (1989) 86: 1173-1177.
Landegren, Ulf et al., "A Ligase-Mediated Gene Detection Technique," Science (1988) 241: 1077-1080.
Nielsen, Peter E. et al., "Sequence-Selective Recognition of DNA by Strand Displacement with a Thymine-Substituted Polyamide," Science (1991) 254: 1497-1500.
Wu, Dan Y. and Wallace, Bruce R., "The Ligation Amplification Reaction (LAR)-Amplificatin of Specific DNA Sequences Using Sequential Rounds of Template-Dependent Ligation," Genomics (1989) 4: 560-569.
European Extended Search Report; Application No. EP 06768500.8 (EP regional application of PCT/KR2006001829) dated Jun. 15, 2009.
Cambien, Francois et al., Sequence diversity in 36 candidate genes for cardiovascular disorders, Am J Hum Genet. Jul. 1999; 65(1): pp. 183-191.
Gibbons, Gary H. et al., Genetic Markers—Progress and Potential for Cardiovascular Disease, Circulation, 2004;109 [Suppl. IV]:IV-47-IV-58.
European Office Action for Application No. 06768500.8 dated Sep. 4, 2009.

* cited by examiner

Primary Examiner—Jehanne S Sitton
(74) Attorney, Agent, or Firm—Cantor Colburn LLP

(57) ABSTRACT

A multiple single nucleotide polymorphism (multi-SNP) marker for cardiovascular disease diagnosis and a method of diagnosing cardiovascular disease are provided. Also, sets of polynucleotides, a microarray, and a kit including the microarray are provided.

6 Claims, No Drawings

SEQUENCE LISTING

```
<160> NUMBER OF SEQ ID NOS: 140

<210> SEQ ID NO 1
<211> LENGTH: 201
<212> TYPE: DNA
<213> ORGANISM: Homo sapiens

<400> SEQUENCE: 1
caccacatct cctgccccca tcccaagcaa gaggaacaag ggaagcccca gtgtacatgt      60
caaagagggc tgcaagctct gggcctcctg gaagccctaa wcttcctcca ggcaagaatc     120
tcttgcttct tgtcctttgt aaatctcacc tccttgcttt tagagatcca ggtttctgcc    180
ctctccctct cagcaaatct t                                               201

<210> SEQ ID NO 2
<211> LENGTH: 201
<212> TYPE: DNA
<213> ORGANISM: Homo sapiens

<400> SEQUENCE: 2
tggtgctgag tgcagctgga gatgccctgg ggtactacaa tgggaagtgg gagttcctcc      60
aggatgggga gaagatacac cggcagttgg cccagctggg yggcttggat gccctagacg    120
tgggaaggtg gagagttagt gacgacacag tgatgcactt ggccacagca gaagctcttg    180
tggaagctgg gaaagcccct a                                               201

<210> SEQ ID NO 3
<211> LENGTH: 201
<212> TYPE: DNA
<213> ORGANISM: Homo sapiens

<400> SEQUENCE: 3
tgagagagac aagaccgaga aggagctgag ggggcccccg gcttaccttc tgctgtagta      60
cccagaacaa cggcagcttc ttcccccggc cgggtcacga kgccctattt atagctgagg    120 ggtgggatg gagctgttcc caggctgcct gtgcacaggc tggagaggag ggttacatca    180
cttggccaga ccacaggctg g                                               201

<210> SEQ ID NO 4
<211> LENGTH: 176
<212> TYPE: DNA
<213> ORGANISM: Homo sapiens

<400> SEQUENCE: 4
gttctatatc tttatatttt caagtgacat gaaaacttct ttcttctctt gatcaaacag      60
ttgccatgac agagcygtct gtttgcctca ctggcactta tgtactaaat atgatgatcc    120
ctttagaaac ttactcggat ttgtattgtt tattatttgc tgaataagga caattt        176

<210> SEQ ID NO 5
<211> LENGTH: 201
<212> TYPE: DNA
<213> ORGANISM: Homo sapiens
```

```
<400> SEQUENCE: 5
gaccttgtga tctgccgccc tcagcctcct gaagtgctgg gattataggc gtgagccact    60
gtgcctggtc cttttttactt tttatttaca ttctctggac stcctagtct gtagtcttat   120
gccaacttta cagaagaaag gctagagttt cagaggagtt gtacaagtgg tccaaggtct   180
cacactagta agcagtagag a                                              201

<210> SEQ ID NO 6
<211> LENGTH: 170
<212> TYPE: DNA
<213> ORGANISM: Homo sapiens

<400> SEQUENCE: 6 tttcccttc tgggccagtg agaatcttcc aggccacacc catagtacaa ggacttcacc     60
agtcacggcc ttcctcatct gtttctctag cctcctcttg mtagcgtcca tgctctcatt   120
tcatcatcca tgggacttct tgtatgcctt tccctcttcc tgaaccttcc                170

<210> SEQ ID NO 7
<211> LENGTH: 201
<212> TYPE: DNA
<213> ORGANISM: Homo sapiens

<400> SEQUENCE: 7
ttcaatggta atgcaaagct aaatatcaat taattaaaga gttctggggg tggaaaaggg     60
gacaagggaa aggaaccact cttggttctt acaagatgga rtttgcaaga gaacttaaat   120
tacaaaggaa aaatggcatt aaattaatat ctaatttcta agctagttga ccaaattatt   180
tgaggcttat tggcgttctc t                                              201

<210> SEQ ID NO 8
<211> LENGTH: 185
<212> TYPE: DNA
<213> ORGANISM: Homo sapiens

<400> SEQUENCE: 8
tgcaaagttt attggaaaat caaaattttt ttattaattt actggatttc ctatacctaa     60
caatccttaa aacaactatc aacasctgca acacaaacca caggcaaaat gaaaaacaga   120
tgccccagac agcaccccac cacatggcac acacttaata aggaacaaaa tcctacaggg   180
tgctg                                                                185

<210> SEQ ID NO 9
<211> LENGTH: 101
<212> TYPE: DNA
<213> ORGANISM: Homo sapiens

<400> SEQUENCE: 9
cttttttccc ctcctcttac cccgtatagg cagaagacac acatttggcc rtaagtgtga     60
attgccattg atgagtttca aagtcagtta tcatgccttg a                        101

<210> SEQ ID NO 10
<211> LENGTH: 135
<212> TYPE: DNA
<213> ORGANISM: Homo sapiens

<400> SEQUENCE: 10
caaattcaaa gtctgtgtgc tcatgcactc gctgyggtgc ctcagacaaa ccaaacctaa     60
aagaagctgc aatggtggct tgaaatatta aaatatgaca aatcacacag gctgagaatt   120
```
tctgttaaca taatc 135

<210> SEQ ID NO 11
<211> LENGTH: 201
<212> TYPE: DNA
<213> ORGANISM: Homo sapiens

<400> SEQUENCE: 11
gctgtggatt ttgagagtca ggggaggggt gtgtgtgtga ggggtggct tactccggag      60 tctgggattc atcccgtcat ttcctttcaat aaataattat yggatagcta ctttgtgaca   120
gggtctgtgc tgggctctgg gggcaaagct gtcatgggtg tcacctgcat agcatgtagc   180
catgtagcca tggcctagga a                                              201

<210> SEQ ID NO 12
<211> LENGTH: 201
<212> TYPE: DNA
<213> ORGANISM: Homo sapiens

<400> SEQUENCE: 12
ggaggattaa atgcccctta gttgcttagt aaataaacaa tagatattgt tagttttaga    60
ccagaaaaaa cacacattct ttaaaaggcc accagataat sctacatagg ttgtttaggg   120
taaatccttg tatgtcttta ataaggtaag tttggggaaa ctaacaaaac atatttgtct   180
tgctgttttg tattaataga g                                              201

<210> SEQ ID NO 13
<211> LENGTH: 201
<212> TYPE: DNA
<213> ORGANISM: Homo sapiens

<400> SEQUENCE: 13
gggacagccc ttcctgtgtg tacagcgggc ccacggccac cacactaccc tctggagtga    60
actgactgcc gcgaggcctg gggagctggc tcaccacctg kcctccgccg ttcaccctgt   120
ccactgcaga aacgacctcc taccctcaaga ccggccccca accccatgc acaggagccc   180 agccctcttg ggccccggct c                                              201

<210> SEQ ID NO 14
<211> LENGTH: 201
<212> TYPE: DNA
<213> ORGANISM: Homo sapiens

<400> SEQUENCE: 14
tcaaggagca aagctagtct gtgagcaaca agctacagca tcaaaagata caagcaagtg    60
tgggtttggg agccaggttt ctgcctggtg tgtgagtctg rgaaagtcag ttccttcct   120 tgagccttgg tttcttcatt tttcttgtga ggattagagg agattagtga ctggcacata   180
ataagcagcc agcaaatggc c                                              201

<210> SEQ ID NO 15
<211> LENGTH: 201
<212> TYPE: DNA
<213> ORGANISM: Homo sapiens

<400> SEQUENCE: 15
gcatagtact cagactcatt gaaagtttat agaatttggc ctgtgtggaa aactctgtgc    60
tccaagtaca acaactaact gaattctcta atttaaacaa stttgaaggg aagtgaaagg   120
ttataaaatg atacagactc ataccgcaga atcaccttaa aatgcagctg ttggagaaaa    180
aaaaaaagga agctttatgc t                                              201

<210> SEQ ID NO 16
<211> LENGTH: 201
<212> TYPE: DNA
<213> ORGANISM: Homo sapiens
<220> FEATURE:
<221> NAME/KEY: misc_feature
<222> LOCATION: (180)..(180)
<223> OTHER INFORMATION: n is a, c, g, or t

<400> SEQUENCE: 16
agaggcggcg gctccggaac gagctgctcc cacagcccct ccgctcctcg ccgtctcgcc    60
ttcgtcccca gcttacccag ttctgcgcgt tattgctcag yttgactttc ttgcacaggc    120
tcccggggat ctccatgacc gcggagcgcg ctgagcagcc ggggttctct gcgccgggan    180
ggtagcaaga ggagggcagg c                                              201

<210> SEQ ID NO 17
<211> LENGTH: 151
<212> TYPE: DNA
<213> ORGANISM: Homo sapiens

<400> SEQUENCE: 17
gattacaggc gtgagccacg gcacctggag agaaaaaagc ttctttaatg acgacctcaa    60
cataatttac atggagaagt ttcttaggtg gaaaaccgat ytgtatggtc ctcagaatgt    120
aacctacagg ttcttgccct cagaaaaatg c                                   151

<210> SEQ ID NO 18
<211> LENGTH: 201
<212> TYPE: DNA
<213> ORGANISM: Homo sapiens

<400> SEQUENCE: 18
cctccaaagg ggaaaccctg ccctcctggg cagacctttt ctttaagcgg cttctagatc    60
caccagggaa gaggggagac agcaagtgga acagacccag scaggaaagc ccgccctagt    120
ggctgcacac ccattccacc tccaggaaga tgtcacaact cctgttacgg tggcaataac    180
acaggccgga gcccagccaa g                                              201

<210> SEQ ID NO 19
<211> LENGTH: 185
<212> TYPE: DNA
<213> ORGANISM: Homo sapiens

<400> SEQUENCE: 19 ctgcttttc tcttggggct ggtagaagga ataaagagag tgagtgtgaa acagccccg      60 cccctttgca cctgtgttct ctgtygacgt ggactgacac agttggtatt ttgctgggtg    120
tctctggacc ctttaacaca cactccatag atctgtgttc tgtgtctgcc tgcagagcct    180
ccacc                                                                185

<210> SEQ ID NO 20
<211> LENGTH: 201
<212> TYPE: DNA
<213> ORGANISM: Homo sapiens

<400> SEQUENCE: 20
tgatttgatt ttatccagtg ttgcaaactg ggtttcgtaa gtgactcttt tgtaaggagt    60

```
ttcagtgcac cccgtctgca acccatgcat atcttattta mccccaagct tctaaggtag    120
aatcctactt ttttcaagtg ctattgatta gttgcctgtt tagacttttg ttatatgatt    180
taaaatttta aaatgataa t                                                201
```

<210> SEQ ID NO 21
<211> LENGTH: 201
<212> TYPE: DNA
<213> ORGANISM: Homo sapiens

<400> SEQUENCE: 21

```
gggtatgttg gtcaagtatc ttgagcagat aaattttact aatagaaaag gaacaataat    60
gatactgttg tatgtgtgtg cacgcacaca cactaacacg ygcacaggaa agaaagaaaa    120
atgtactctg gcccatccat tctgtgccaa tttcccctgt tgggacttag tttaatccag    180 cctttttggct tgttcatcat a                                              201
```

<210> SEQ ID NO 22
<211> LENGTH: 201
<212> TYPE: DNA
<213> ORGANISM: Homo sapiens

<400> SEQUENCE: 22

```
tttttctgtt ctccatttcc tttaagtttg tttttagata cactgcattg caagtatgtg    60
tggtacagta aaatgttgct aattgtatct gcgctgataa satgccattt gctctaggtc    120
agtttcctac cccctccccc aactattcct agccagtggt agcatgcttc ttacttccaa    180
atatatgtgt gtgtgtgtgt g                                              201
```

<210> SEQ ID NO 23
<211> LENGTH: 201
<212> TYPE: DNA
<213> ORGANISM: Homo sapiens

<400> SEQUENCE: 23

```
gaagtattgg gaaagatgt ccttaaccga aattataagc acatttagaa ggaaacaaaa     60
taaaaagagt tttcactcat tccagaattt tacaggcaat rgctattttc taatataatt    120
attttagcaa ataatgttt gatttggatg tgctatgaca gtatcttcca tatttcattt     180
tattcattac atatttctga t                                              201
```

<210> SEQ ID NO 24
<211> LENGTH: 201
<212> TYPE: DNA
<213> ORGANISM: Homo sapiens

<400> SEQUENCE: 24

```
gctccatgga cttagtacct gggtgaccac cgtcagcaga aagcatgtt tggaagacag     60 agaaccaatg agggatgttt cacactcttg aggagtttgc mgtcaaaaag caaagcagga    120
taagcaaaaa atgcatgtcc tcaaacccca gataacaaac acaaaacatc atagatagaa    180
ccagagctga ggtagataca c                                              201
```

<210> SEQ ID NO 25
<211> LENGTH: 201
<212> TYPE: DNA
<213> ORGANISM: Homo sapiens

<400> SEQUENCE: 25

```
ttaggaaatt tcaatggag aaaataagtt ccaaaagtca ttctttctca gattaagatg    60
tcttgggttt cagtttactt ctttaaagaa agattcagag ytagtactga ggacccagac   120
tttcttgatg tgggaaatag ataatttct gttctgttga cattttttct ctctcttctc    180
tcattttcaa agtacagttc c                                             201

<210> SEQ ID NO 26
<211> LENGTH: 201
<212> TYPE: DNA
<213> ORGANISM: Homo sapiens

<400> SEQUENCE: 26
tagattaatt ggtgatttcg tacaataatt tgggagaaat taacattgca ttttttatgtc   60 tttcgacgtg ataaatctcc tgatactcaa atgttctgtt ktgtacttca acaagtttca   120
taattttgtt cttatttaaa attcatgtaa atcttttct ggacttattt cttcatattg    180
tatagctgat gttactatca t                                             201

<210> SEQ ID NO 27
<211> LENGTH: 201
<212> TYPE: DNA
<213> ORGANISM: Homo sapiens

<400> SEQUENCE: 27
ataccattcc aaaaaatcta aatatgcat tactgaagat tcttttggat aagaaaaaaa    60
aggaaatgta ctctgggcat gaacaataat ttttctgaag mcttaattct ttctaaaatg   120
gaaaactatt ggaaaactaa cctgcatggt tctaagaaca ttttccacaa aaaaaaaaa   180 taataattca attcaaagat c                                             201

<210> SEQ ID NO 28
<211> LENGTH: 201
<212> TYPE: DNA
<213> ORGANISM: Homo sapiens

<400> SEQUENCE: 28
aaagctgagt aagcacctat agtaacaggt aacaaagtat tctagggatc agctgctgtg    60
agttagttca caagtgcttt aagtacgtgt taatcaaaga ygatgtattt ttcatttctg   120
acaataaaca tctggggcat cctacatttt tcctgggcaa tttgcctta tcattatatt    180 ttaatctctg atgcaatctt t                                             201

<210> SEQ ID NO 29
<211> LENGTH: 201
<212> TYPE: DNA
<213> ORGANISM: Homo sapiens

<400> SEQUENCE: 29
atgggagaga acaatagctc cctaggcaag aaaaagttac atatttgcaa aagccaagtt    60
ccagtgaagg agaataggta cagggattgc tctgagaagt ygtttgggag actggagaat   120
ttgctgtaca tgaagactac aatgagttgt gtttaagagt ctggtgcttt ggaatcagaa   180
agtttgagtt taaatctta t                                              201

<210> SEQ ID NO 30
<211> LENGTH: 201
<212> TYPE: DNA
<213> ORGANISM: Homo sapiens

<400> SEQUENCE: 30
```

```
tgatatgact tcttgctagt gatttgtttc caggatctcc tcctagtata tccaaggcaa    60
tgtactattt catgggaggg gaatggcttt ataaagcttt ygtatctact ctctcacagt   120
aatttctggg gagtctgggg atttggatga caactttctt catttccaaa tctgaatcag   180
cattctggtt tcttggctat c                                             201

<210> SEQ ID NO 31
<211> LENGTH: 201
<212> TYPE: DNA
<213> ORGANISM: Homo sapiens

<400> SEQUENCE: 31
acagggatgg ggtcagattt ttccatcctc tggtggcagg gttggaggcc tgacaagaga    60
tcctctcttt ccctccttcc cccttccca aggagcttca kccaagctga ggtcacctgg   120
agctgtgctc tgcactgtgc aagctcagca gccgggccct ggggcaggta aagctgtgga   180
ttcccaggtt ctggtgcctg c                                             201

<210> SEQ ID NO 32
<211> LENGTH: 201
<212> TYPE: DNA
<213> ORGANISM: Homo sapiens

<400> SEQUENCE: 32
cagagacctg gtcctaaatc tgtgtgactt ttgcgaaatc cttttgcctc acagagctct    60
aggttcttat ctgtcaaaca ggaaccagac catcagatcc rtagagatcc aaccaatgaa   120
ggagacttcg aaaacttcac attgccgtgt caatgtgagg ttgctggatg gttatgacaa   180
gaaatcacat taaattcact g                                             201

<210> SEQ ID NO 33
<211> LENGTH: 201
<212> TYPE: DNA
<213> ORGANISM: Homo sapiens

<400> SEQUENCE: 33
aaacccacag aaccaggcaa gagaccacct aaaattttgt tcacctaaaa ttctagagtt    60
ctttgagcaa accaaatgag tggttgtatc attttaaatt macagaata gataggaagt   120 ctaggtcatt aacataattt gtgctctcag ttcatttttc aagtgggctt cctattgcat   180
ttttcttctg attcagttga g                                             201

<210> SEQ ID NO 34
<211> LENGTH: 201
<212> TYPE: DNA
<213> ORGANISM: Homo sapiens

<400> SEQUENCE: 34
gtatagaatg tctttccttc ccctacccaa cctgacaagc tcttctgctg cctccaagac    60
ccatttcaga tgacttctct tccagaaaaa ccttccttag wtcctgagac cgagctagtc   120
tgtcctttct gtgtgctccc acaaagcttt gttaaacact agtcacctca actatatgat   180
attctctctc tgactacctc a                                             201

<210> SEQ ID NO 35
<211> LENGTH: 201
<212> TYPE: DNA
<213> ORGANISM: Homo sapiens
```

-continued

<400> SEQUENCE: 35
gcaccattct caccctccta catcactctt gccagaaatt tgatgtacat ttgctattta    60
taagtaccct ttaggcactg tggattaaaa aaatacaaaa wgtgatggac agtgaactaa   120
agaacatttg gccaatgatt ccaaggttca atgaagctta gtacagttat tattattcaa   180
aatttagtac tttgtctttc a                                              201

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
acgttggatg ccccagtgta catgtcaaag                                      30

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
acgttggatg agcaagagat tcttgcctgg                                      30

<210> SEQ ID NO 38
<211> LENGTH: 17
<212> TYPE: DNA
<213> ORGANISM: Artificial Sequence
<220> FEATURE:
<223> OTHER INFORMATION: primer

<400> SEQUENCE: 38
cctcctggaa gccctaa                                                    17

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
acgttggatg tgtgtcgtca ctaactctcc                                      30

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
acgttggatg agaagataca ccggcagttg                                      30

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
acgtctaggg catccaagcc                                                20

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
acgttggatg tgtagtaccc agaacaacgg                                      30

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
acgttggatg agcctgggaa cagctccatc                                      30

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
ttcccccggc cgggtcacga                                                 20

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
acgttggatg ctcttgatca aacagttgcc                                      30

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
acgttggatg gtacataagt gccagtgagg                                      30

<210> SEQ ID NO 47
<211> LENGTH: 17
<212> TYPE: DNA
<213> ORGANISM: Artificial Sequence
<220> FEATURE:
<223> OTHER INFORMATION: primer

<400> SEQUENCE: 47
agttgccatg acagagc                                                    17

<210> SEQ ID NO 48
<211> LENGTH: 31
<212> TYPE: DNA

<210> SEQ ID NO 48
<211> LENGTH: 31
<212> TYPE: DNA
<213> ORGANISM: Artificial Sequence
<220> FEATURE:
<223> OTHER INFORMATION: primer

<400> SEQUENCE: 48
acgttggatg cctttcttct gtaaagttgg c        31

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
acgttggatg ctgtgcctgg tccttttac        30

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
tggcataaga ctacagacta gga        23

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
acgttggatg aggaagaggg aaaggcatac        30

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
acgttggatg cctcatctgt ttctctagcc        30

<210> SEQ ID NO 53
<211> LENGTH: 17
<212> TYPE: DNA
<213> ORGANISM: Artificial Sequence
<220> FEATURE:
<223> OTHER INFORMATION: primer

<400> SEQUENCE: 53
tgagagcatg gacgcta        17

<210> SEQ ID NO 54
<211> LENGTH: 30
<212> TYPE: DNA
<213> ORGANISM: Artificial Sequence
<220> FEATURE:
<223> OTHER INFORMATION: primer

<400> SEQUENCE: 54
acgttggatg gaaccactct tggttcttac        30

<210> SEQ ID NO 55
<211> LENGTH: 30
<212> TYPE: DNA
<213> ORGANISM: Artificial Sequence
<220> FEATURE:
<223> OTHER INFORMATION: primer

<400> SEQUENCE: 55
acgttggatg ggtcaactag cttagaaatt                                      30

<210> SEQ ID NO 56
<211> LENGTH: 18
<212> TYPE: DNA
<213> ORGANISM: Artificial Sequence
<220> FEATURE:
<223> OTHER INFORMATION: primer

<400> SEQUENCE: 56
tggttcttac aagatgga                                                   18

<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
acgttggatg cattttgcct gtggtttgtg                                      30

<210> SEQ ID NO 58
<211> LENGTH: 30
<212> TYPE: DNA
<213> ORGANISM: Artificial Sequence
<220> FEATURE:
<223> OTHER INFORMATION: primer

<400> SEQUENCE: 58
acgttggatg ctggatttcc tatacctaac                                      30

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
gcctgtggtt tgtgttgcag                                                 20

<210> SEQ ID NO 60
<211> LENGTH: 30
<212> TYPE: DNA
<213> ORGANISM: Artificial Sequence
<220> FEATURE:
<223> OTHER INFORMATION: primer

<400> SEQUENCE: 60
acgttggatg ttttcccct cctcttaccc                                       30

<210> SEQ ID NO 61
<211> LENGTH: 30
<212> TYPE: DNA
<213> ORGANISM: Artificial Sequence
<220> FEATURE:

-continued

<223> OTHER INFORMATION: primer

<400> SEQUENCE: 61
acgttggatg ctttgaaact catcaatggc                                30

<210> SEQ ID NO 62
<211> LENGTH: 17
<212> TYPE: DNA
<213> ORGANISM: Artificial Sequence
<220> FEATURE:
<223> OTHER INFORMATION: primer

<400> SEQUENCE: 62
aagacacaca tttggcc                                              17

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
acgttggatg tttcaagcca ccattgcagc                                30

<210> SEQ ID NO 64
<211> LENGTH: 30
<212> TYPE: DNA
<213> ORGANISM: Artificial Sequence
<220> FEATURE:
<223> OTHER INFORMATION: primer

<400> SEQUENCE: 64
acgttggatg tcaaagtctg tgtgctcatg                                30

<210> SEQ ID NO 65
<211> LENGTH: 17
<212> TYPE: DNA
<213> ORGANISM: Artificial Sequence
<220> FEATURE:
<223> OTHER INFORMATION: primer

<400> SEQUENCE: 65
ggtttgtctg aggcacc                                              17

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
acgttggatg cagaccctgt cacaaagtag                                30

<210> SEQ ID NO 67
<211> LENGTH: 30
<212> TYPE: DNA
<213> ORGANISM: Artificial Sequence
<220> FEATURE:
<223> OTHER INFORMATION: primer

<400> SEQUENCE: 67
acgttggatg gggattcatc ccgtcatttc                                30

<210> SEQ ID NO 68
<211> LENGTH: 18
<212> TYPE: DNA
<213> ORGANISM: Artificial Sequence
<220> FEATURE:
<223> OTHER INFORMATION: primer

<400> SEQUENCE: 68
gtcacaaagt agctatcc                                            18

<210> SEQ ID NO 69
<211> LENGTH: 31
<212> TYPE: DNA
<213> ORGANISM: Artificial Sequence
<220> FEATURE:
<223> OTHER INFORMATION: primer

<400> SEQUENCE: 69
acgttggatg cacattcttt aaaaggccac c                             31

<210> SEQ ID NO 70
<211> LENGTH: 31
<212> TYPE: DNA
<213> ORGANISM: Artificial Sequence
<220> FEATURE:
<223> OTHER INFORMATION: primer

<400> SEQUENCE: 70
acgttggatg gttagtttcc ccaaacttac c                             31

<210> SEQ ID NO 71
<211> LENGTH: 17
<212> TYPE: DNA
<213> ORGANISM: Artificial Sequence
<220> FEATURE:
<223> OTHER INFORMATION: primer

<400> SEQUENCE: 71
aaaggccacc agataat                                             17

<210> SEQ ID NO 72
<211> LENGTH: 30
<212> TYPE: DNA
<213> ORGANISM: Artificial Sequence
<220> FEATURE:
<223> OTHER INFORMATION: primer

<400> SEQUENCE: 72
acgttggatg cctctggagt gaactgactg                               30

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
acgttggatg tcgtttctgc agtggacagg                               30

<210> SEQ ID NO 74
<211> LENGTH: 20
<212> TYPE: DNA
<213> ORGANISM: Artificial Sequence
<220> FEATURE:
<223> OTHER INFORMATION: primer

```
<400> SEQUENCE: 74
gggagctggc tcaccacctg                                          20

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
acgttggatg acaagcaagt gtgggtttgg                               30

<210> SEQ ID NO 76
<211> LENGTH: 30
<212> TYPE: DNA
<213> ORGANISM: Artificial Sequence
<220> FEATURE:
<223> OTHER INFORMATION: primer

<400> SEQUENCE: 76
acgttggatg caaggctcaa ggaaaggaac                               30

<210> SEQ ID NO 77
<211> LENGTH: 20
<212> TYPE: DNA
<213> ORGANISM: Artificial Sequence
<220> FEATURE:
<223> OTHER INFORMATION: primer

<400> SEQUENCE: 77
ctgcctggtg tgtgagtctg                                          20

<210> SEQ ID NO 78
<211> LENGTH: 30
<212> TYPE: DNA
<213> ORGANISM: Artificial Sequence
<220> FEATURE:
<223> OTHER INFORMATION: primer

<400> SEQUENCE: 78
acgttggatg ctgcggtatg agtctgtatc                               30

<210> SEQ ID NO 79
<211> LENGTH: 30
<212> TYPE: DNA
<213> ORGANISM: Artificial Sequence
<220> FEATURE:
<223> OTHER INFORMATION: primer

<400> SEQUENCE: 79
acgttggatg ctctgtgctc caagtacaac                               30

<210> SEQ ID NO 80
<211> LENGTH: 21
<212> TYPE: DNA
<213> ORGANISM: Artificial Sequence
<220> FEATURE:
<223> OTHER INFORMATION: primer

<400> SEQUENCE: 80
aacctttcac ttcccttcaa a                                        21

<210> SEQ ID NO 81
<211> LENGTH: 29
```

<210> SEQ ID NO 81
<211> LENGTH: 29
<212> TYPE: DNA
<213> ORGANISM: Artificial Sequence
<220> FEATURE:
<223> OTHER INFORMATION: primer

<400> SEQUENCE: 81
acgttggatg ctccgcggtc atggagatc                                    29

<210> SEQ ID NO 82
<211> LENGTH: 30
<212> TYPE: DNA
<213> ORGANISM: Artificial Sequence
<220> FEATURE:
<223> OTHER INFORMATION: primer

<400> SEQUENCE: 82
acgttggatg ttacccagtt ctgcgcgtta                                   30

<210> SEQ ID NO 83
<211> LENGTH: 17
<212> TYPE: DNA
<213> ORGANISM: Artificial Sequence
<220> FEATURE:
<223> OTHER INFORMATION: primer

<400> SEQUENCE: 83
ctgtgcaaga aagtcaa                                                 17

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
acgttggatg tttctgaggg caagaacctg                                   30

<210> SEQ ID NO 85
<211> LENGTH: 30
<212> TYPE: DNA
<213> ORGANISM: Artificial Sequence
<220> FEATURE:
<223> OTHER INFORMATION: primer

<400> SEQUENCE: 85
acgttggatg tggagaagtt tcttaggtgg                                   30

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
ttacattctg aggaccatac a                                            21

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87

```
acgttggatg ggagacagca agtggaacag                                    30

<210> SEQ ID NO 88
<211> LENGTH: 30
<212> TYPE: DNA
<213> ORGANISM: Artificial Sequence
<220> FEATURE:
<223> OTHER INFORMATION: primer

<400> SEQUENCE: 88
acgttggatg atcttcctgg aggtggaatg                                    30

<210> SEQ ID NO 89
<211> LENGTH: 20
<212> TYPE: DNA
<213> ORGANISM: Artificial Sequence
<220> FEATURE:
<223> OTHER INFORMATION: primer

<400> SEQUENCE: 89
agcaagtgga acagacccag                                               20

<210> SEQ ID NO 90
<211> LENGTH: 30
<212> TYPE: DNA
<213> ORGANISM: Artificial Sequence
<220> FEATURE:
<223> OTHER INFORMATION: primer

<400> SEQUENCE: 90
acgttggatg gagacaccca gcaaaatacc                                    30

<210> SEQ ID NO 91
<211> LENGTH: 30
<212> TYPE: DNA
<213> ORGANISM: Artificial Sequence
<220> FEATURE:
<223> OTHER INFORMATION: primer

<400> SEQUENCE: 91
acgttggatg agagtgagtg tgaaacagcc                                    30

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
caactgtgtc agtccacgtc                                               20

<210> SEQ ID NO 93
<211> LENGTH: 31
<212> TYPE: DNA
<213> ORGANISM: Artificial Sequence
<220> FEATURE:
<223> OTHER INFORMATION: primer

<400> SEQUENCE: 93
acgttggatg gtaggattct accttagaag c                                  31

<210> SEQ ID NO 94
<211> LENGTH: 30
<212> TYPE: DNA
<213> ORGANISM: Artificial Sequence
```

```
<220> FEATURE:
<223> OTHER INFORMATION: primer

<400> SEQUENCE: 94
acgttggatg taaggagttt cagtgcaccc                                    30

<210> SEQ ID NO 95
<211> LENGTH: 17
<212> TYPE: DNA
<213> ORGANISM: Artificial Sequence
<220> FEATURE:
<223> OTHER INFORMATION: primer

<400> SEQUENCE: 95
accttagaag cttgggg                                                  17

<210> SEQ ID NO 96
<211> LENGTH: 30
<212> TYPE: DNA
<213> ORGANISM: Artificial Sequence
<220> FEATURE:
<223> OTHER INFORMATION: primer

<400> SEQUENCE: 96
acgttggatg ctgttgtatg tgtgtgcacg                                    30

<210> SEQ ID NO 97
<211> LENGTH: 30
<212> TYPE: DNA
<213> ORGANISM: Artificial Sequence
<220> FEATURE:
<223> OTHER INFORMATION: primer

<400> SEQUENCE: 97
acgttggatg attggcacag aatggatggg                                    30

<210> SEQ ID NO 98
<211> LENGTH: 17
<212> TYPE: DNA
<213> ORGANISM: Artificial Sequence
<220> FEATURE:
<223> OTHER INFORMATION: primer

<400> SEQUENCE: 98
gcacacacac taacacg                                                  17

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
acgttggatg tgcaagtatg tgtggtacag                                    30

<210> SEQ ID NO 100
<211> LENGTH: 30
<212> TYPE: DNA
<213> ORGANISM: Artificial Sequence
<220> FEATURE:
<223> OTHER INFORMATION: primer

<400> SEQUENCE: 100
acgttggatg gtaggaaact gacctagagc                                    30
```

```
<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
aattgtatct gcgctgataa                                              20

<210> SEQ ID NO 102
<211> LENGTH: 30
<212> TYPE: DNA
<213> ORGANISM: Artificial Sequence
<220> FEATURE:
<223> OTHER INFORMATION: primer

<400> SEQUENCE: 102
acgttggatg agagttttca ctcattccag                                   30

<210> SEQ ID NO 103
<211> LENGTH: 30
<212> TYPE: DNA
<213> ORGANISM: Artificial Sequence
<220> FEATURE:
<223> OTHER INFORMATION: primer

<400> SEQUENCE: 103
acgttggatg gatactgtca tagcacatcc                                   30

<210> SEQ ID NO 104
<211> LENGTH: 20
<212> TYPE: DNA
<213> ORGANISM: Artificial Sequence
<220> FEATURE:
<223> OTHER INFORMATION: primer

<400> SEQUENCE: 104
tccagaattt tacaggcaat                                              20

<210> SEQ ID NO 105
<211> LENGTH: 30
<212> TYPE: DNA
<213> ORGANISM: Artificial Sequence
<220> FEATURE:
<223> OTHER INFORMATION: primer

<400> SEQUENCE: 105
acgttggatg gggtttgagg acatgcattt                                   30

<210> SEQ ID NO 106
<211> LENGTH: 30
<212> TYPE: DNA
<213> ORGANISM: Artificial Sequence
<220> FEATURE:
<223> OTHER INFORMATION: primer

<400> SEQUENCE: 106
acgttggatg cagagaacca atgagggatg                                   30

<210> SEQ ID NO 107
<211> LENGTH: 17
<212> TYPE: DNA
<213> ORGANISM: Artificial Sequence
<220> FEATURE:
<223> OTHER INFORMATION: primer
```

-continued

```
<400> SEQUENCE: 107
ctgctttgct ttttgac                                                  17

<210> SEQ ID NO 108
<211> LENGTH: 30
<212> TYPE: DNA
<213> ORGANISM: Artificial Sequence
<220> FEATURE:
<223> OTHER INFORMATION: primer

<400> SEQUENCE: 108
acgttggatg tcaagaaagt ctgggtcctc                                    30

<210> SEQ ID NO 109
<211> LENGTH: 31
<212> TYPE: DNA
<213> ORGANISM: Artificial Sequence
<220> FEATURE:
<223> OTHER INFORMATION: primer

<400> SEQUENCE: 109
acgttggatg ctcagattaa gatgtcttgg g                                  31

<210> SEQ ID NO 110
<211> LENGTH: 17
<212> TYPE: DNA
<213> ORGANISM: Artificial Sequence
<220> FEATURE:
<223> OTHER INFORMATION: primer

<400> SEQUENCE: 110
ctgggtcctc agtacta                                                  17

<210> SEQ ID NO 111
<211> LENGTH: 30
<212> TYPE: DNA
<213> ORGANISM: Artificial Sequence
<220> FEATURE:
<223> OTHER INFORMATION: primer

<400> SEQUENCE: 111
acgttggatg cgtgataaat ctcctgatac                                    30

<210> SEQ ID NO 112
<211> LENGTH: 31
<212> TYPE: DNA
<213> ORGANISM: Artificial Sequence
<220> FEATURE:
<223> OTHER INFORMATION: primer

<400> SEQUENCE: 112
acgttggatg gtccagaaaa agatttacat g                                  31

<210> SEQ ID NO 113
<211> LENGTH: 23
<212> TYPE: DNA
<213> ORGANISM: Artificial Sequence
<220> FEATURE:
<223> OTHER INFORMATION: primer

<400> SEQUENCE: 113
tcctgatact caaatgttct gtt                                           23

<210> SEQ ID NO 114
```

```
<211> LENGTH: 30
<212> TYPE: DNA
<213> ORGANISM: Artificial Sequence
<220> FEATURE:
<223> OTHER INFORMATION: primer

<400> SEQUENCE: 114
acgttggatg ggaaatgtac tctgggcatg                                        30

<210> SEQ ID NO 115
<211> LENGTH: 30
<212> TYPE: DNA
<213> ORGANISM: Artificial Sequence
<220> FEATURE:
<223> OTHER INFORMATION: primer

<400> SEQUENCE: 115
acgttggatg tgttcttaga accatgcagg                                        30

<210> SEQ ID NO 116
<211> LENGTH: 23
<212> TYPE: DNA
<213> ORGANISM: Artificial Sequence
<220> FEATURE:
<223> OTHER INFORMATION: primer

<400> SEQUENCE: 116
catgaacaat aattttctg aag                                                23

<210> SEQ ID NO 117
<211> LENGTH: 30
<212> TYPE: DNA
<213> ORGANISM: Artificial Sequence
<220> FEATURE:
<223> OTHER INFORMATION: primer

<400> SEQUENCE: 117
acgttggatg aatgtaggat gccccagatg                                        30

<210> SEQ ID NO 118
<211> LENGTH: 30
<212> TYPE: DNA
<213> ORGANISM: Artificial Sequence
<220> FEATURE:
<223> OTHER INFORMATION: primer

<400> SEQUENCE: 118
acgttggatg cagctgctgt gagttagttc                                        30

<210> SEQ ID NO 119
<211> LENGTH: 23
<212> TYPE: DNA
<213> ORGANISM: Artificial Sequence
<220> FEATURE:
<223> OTHER INFORMATION: primer

<400> SEQUENCE: 119
ttgtcagaaa tgaaaaatac atc                                               23

<210> SEQ ID NO 120
<211> LENGTH: 30
<212> TYPE: DNA
<213> ORGANISM: Artificial Sequence
<220> FEATURE:
<223> OTHER INFORMATION: primer

<400> SEQUENCE: 120
```
acgttggatg gtacagcaaa ttctccagtc                30

<210> SEQ ID NO 121
<211> LENGTH: 30
<212> TYPE: DNA
<213> ORGANISM: Artificial Sequence
<220> FEATURE:
<223> OTHER INFORMATION: primer

<400> SEQUENCE: 121
acgttggatg aagccaagtt ccagtgaagg                30

<210> SEQ ID NO 122
<211> LENGTH: 17
<212> TYPE: DNA
<213> ORGANISM: Artificial Sequence
<220> FEATURE:
<223> OTHER INFORMATION: primer

<400> SEQUENCE: 122
tctccagtct cccaaac                17

<210> SEQ ID NO 123
<211> LENGTH: 30
<212> TYPE: DNA
<213> ORGANISM: Artificial Sequence
<220> FEATURE:
<223> OTHER INFORMATION: primer

<400> SEQUENCE: 123
acgttggatg ccagactccc cagaaattac                30

<210> SEQ ID NO 124
<211> LENGTH: 30
<212> TYPE: DNA
<213> ORGANISM: Artificial Sequence
<220> FEATURE:
<223> OTHER INFORMATION: primer

<400> SEQUENCE: 124
acgttggatg tgtactattt catgggaggg                30

<210> SEQ ID NO 125
<211> LENGTH: 21
<212> TYPE: DNA
<213> ORGANISM: Artificial Sequence
<220> FEATURE:
<223> OTHER INFORMATION: primer

<400> SEQUENCE: 125
ttactgtgag agagtagata c                21

<210> SEQ ID NO 126
<211> LENGTH: 30
<212> TYPE: DNA
<213> ORGANISM: Artificial Sequence
<220> FEATURE:
<223> OTHER INFORMATION: primer

<400> SEQUENCE: 126
acgttggatg atcctctctt tccctccttc                30

<210> SEQ ID NO 127
<211> LENGTH: 30
<212> TYPE: DNA

```
<213> ORGANISM: Artificial Sequence
<220> FEATURE:
<223> OTHER INFORMATION: primer

<400> SEQUENCE: 127
acgttggatg ttgcacagtg cagagcacag                                          30

<210> SEQ ID NO 128
<211> LENGTH: 20
<212> TYPE: DNA
<213> ORGANISM: Artificial Sequence
<220> FEATURE:
<223> OTHER INFORMATION: primer

<400> SEQUENCE: 128
ccccttccca aggagcttca                                                     20

<210> SEQ ID NO 129
<211> LENGTH: 30
<212> TYPE: DNA
<213> ORGANISM: Artificial Sequence
<220> FEATURE:
<223> OTHER INFORMATION: primer

<400> SEQUENCE: 129
acgttggatg caaacaggaa ccagaccatc                                          30

<210> SEQ ID NO 130
<211> LENGTH: 30
<212> TYPE: DNA
<213> ORGANISM: Artificial Sequence
<220> FEATURE:
<223> OTHER INFORMATION: primer

<400> SEQUENCE: 130
acgttggatg agcaacctca cattgacacg                                          30

<210> SEQ ID NO 131
<211> LENGTH: 17
<212> TYPE: DNA
<213> ORGANISM: Artificial Sequence
<220> FEATURE:
<223> OTHER INFORMATION: primer

<400> SEQUENCE: 131
accagaccat cagatcc                                                        17

<210> SEQ ID NO 132
<211> LENGTH: 30
<212> TYPE: DNA
<213> ORGANISM: Artificial Sequence
<220> FEATURE:
<223> OTHER INFORMATION: primer

<400> SEQUENCE: 132
acgttggatg tgttaatgac ctagacttcc                                          30

<210> SEQ ID NO 133
<211> LENGTH: 30
<212> TYPE: DNA
<213> ORGANISM: Artificial Sequence
<220> FEATURE:
<223> OTHER INFORMATION: primer

<400> SEQUENCE: 133
acgttggatg tgagcaaacc aaatgagtgg                                          30
```

<210> SEQ ID NO 134
<211> LENGTH: 22
<212> TYPE: DNA
<213> ORGANISM: Artificial Sequence
<220> FEATURE:
<223> OTHER INFORMATION: primer

<400> SEQUENCE: 134
tagacttcct atctattcct gt                                            22

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135
acgttggatg caagacccat ttcagatgac                                    30

<210> SEQ ID NO 136
<211> LENGTH: 30
<212> TYPE: DNA
<213> ORGANISM: Artificial Sequence
<220> FEATURE:
<223> OTHER INFORMATION: primer

<400> SEQUENCE: 136
acgttggatg cacagaaagg acagactagc                                    30

<210> SEQ ID NO 137
<211> LENGTH: 21
<212> TYPE: DNA
<213> ORGANISM: Artificial Sequence
<220> FEATURE:
<223> OTHER INFORMATION: primer

<400> SEQUENCE: 137
ttccagaaaa accttcctta g                                             21

<210> SEQ ID NO 138
<211> LENGTH: 30
<212> TYPE: DNA
<213> ORGANISM: Artificial Sequence
<220> FEATURE:
<223> OTHER INFORMATION: primer

<400> SEQUENCE: 138
acgttggatg gaaccttgga atcattggcc                                    30

<210> SEQ ID NO 139
<211> LENGTH: 30
<212> TYPE: DNA
<213> ORGANISM: Artificial Sequence
<220> FEATURE:
<223> OTHER INFORMATION: primer

<400> SEQUENCE: 139
acgttggatg taagtaccct ttaggcactg                                    30

```
<210> SEQ ID NO 140
<211> LENGTH: 17
<212> TYPE: DNA
<213> ORGANISM: Artificial Sequence
<220> FEATURE:
<223> OTHER INFORMATION: primer

<400> SEQUENCE: 140
agttcactgt ccatcac                                                        17
```

MULTIPLE SNP FOR DIAGNOSING CARDIOVASCULAR DISEASE, MICROARRAY AND KIT COMPRISING THE SAME, AND METHOD OF DIAGNOSING CARDIOVASCULAR DISEASE USING THE SAME

CROSS-REFERENCE TO RELATED PATENT APPLICATION

This application claims the benefit of Korean Patent Application Nos. 10-2005-0041653 and 10-2006-0018449, filed on May 18, 2005 and 24 Feb. 2006, in the Korean Intellectual Property Office, the disclosure of each is incorporated herein in its entirety by reference.

BACKGROUND OF THE INVENTION

1. Field of the Invention

The present invention relates to a multiple single nucleotide polymorphism (multi-SNP) marker for diagnosing cardiovascular disease, a method of diagnosing cardiovascular disease using the same, and a set of polynucleotides, a microarray and kit for performing the method.

2. Description of the Related Art

The genomes of all organisms undergo spontaneous mutation in the course of their continuing evolution, generating variant forms of progenitor nucleic acid sequences. (Gusella, Ann. Rev. Biochem. 55, 831-854, 1986). The variant forms of progenitor nucleic acid sequences may confer an evolutionary advantage or disadvantage, or may be neutral relative to a progenitor form. In some instances, a variant form confers a lethal disadvantage and is not transmitted to subsequent generations of the organism. In other instances, a variant form confers an evolutionary advantage to the species and is eventually incorporated into the DNA of most members of the species and effectively becomes the progenitor form. In many instances, both progenitor and variant forms survive and coexist in a species population. The coexistence of multiple forms of a sequence gives rise to polymorphisms.

Several types of polymorphisms are known, including restriction fragment length polymorphism (RFLP), short tandem repeats (STR) and single nucleotide polymorphism (SNP). Among them, a "SNP" is variation of a single nucleotide in a nucleic acid sequence among individuals of the same species. When a SNP occurs in a protein coding sequence of a gene, one of the polymorphic forms may give rise to a non-synonymous codon change, causing expression of a defective or a variant protein. When a SNP occurs in a non-coding sequence of a gene, one of the polymorphic forms may also cause the expression of a defective or variant protein, for example, as a result of defective splicing of mRNA. Other SNPs have no phenotypic effect.

It is estimated that human SNPs occur at a frequency of 1 in every 1,000 bp. When such a SNP induces a phenotypic expression such as the presence or absence of a disease, polynucleotides containing an allele of the SNP can be used as a primer or a probe for diagnosis of the disease. Monoclonal antibodies specifically binding with an amino acid sequence resulting from one of the alleles of the SNP can also be used in the diagnosis of the disease. Currently, research into the nucleotide sequences and functions of SNPs is being performed by many research institutes. The nucleotide sequences and results of other experiments on identified human SNPs have been put in databases to be easily accessible.

Even though findings available to date show that specific SNPs exist in human genomes or cDNAs, the phenotypic effects of SNPs have not been revealed. Functions of most SNPs have not yet been discovered.

Cardiovascular disease is a major cause of death in industrialized countries around the world, and has been a major cause of death in the Republic of Korea since the 1970s. According to the Korea National Statistical Office, in 2003, 22,000 out of 246,000 deaths (9087 per 100,000, or 9.1%) were the result of cardiac disorder and hyperpiesia, which are the third leading cause of death following cancer and cerebrovascular disease.

Cardiovascular disease includes myocardial infarction, angina pectoris, atherosclerosis, hyperpiesia, cardiac failure, aneurysm, arteriosclerosis, embolism, stroke and thrombosis.

Coronary artery disease, which ranks high among cardiovascular diseases, is usually caused by arteriosclerosis, the blocking or narrowing of coronary artery supplying blood to the heart. Blocking of the coronary artery indicates myocardial infarction and narrowing of the coronary artery indicates angina pectoris. Risk factors for coronary artery disease are known to be hyperlipidemia (hypercholesterolemia), hyperpiesia, smoking, diabetes, genetic inheritance, obesity, lack of exercise, stress and menopause. A person having more risk factors for a disease has a higher risk of incidence of the disease. Cardiovascular disease, like other diseases, is also influenced by genetic factors.

The most serious problem in the diagnosis and prognosis of various cardiovascular diseases and associated diseases is that the diagnosis can be performed using a physical technique only when the diseases are at an advanced stage. Currently, X-ray and ultrasonography of the interior of the heart and coronary artery can be used for cardiovascular disease diagnosis, but this diagnosis is only possible at an advanced stage of the disease. However, the developments of recent molecular biological techniques and the primary completion of the human genome project enable the detection of genes or genetic variations directly or indirectly related to a cardiovascular disease. Therefore, early diagnosis of a cardiovascular disease using a genetic factor, instead of using a conventional diagnostic method depending on phenotype or physical characteristics of the disease, has become available.

SUMMARY OF THE INVENTION

As a result of research to find genetic factors associated with the incidence and the probability of cardiovascular disease, the present inventors found that all individuals having cardiovascular disease have the same alleles of specific SNPs, and therefore these SNPs make it possible to predict the incidence, probability of, and genetic susceptibility to cardiovascular disease.

The present invention provides a multiple single nucleotide polymorphism (multi-SNP) marker for cardiovascular disease diagnosis. A multi-SNP marker comprises a set of multiple individual SNPs. The inventors have discovered that particular patterns of genotypes at the set of SNPs comprising a multi-SNP marker are associated with higher incidence or probability of cardiovascular disease The present invention also provides a polynucleotide hybridized with the polynucleotide of a SNP comprising a multi-SNP marker.

The present invention also provides a microarray for cardiovascular disease diagnosis including the polynucleotide, a polypeptide encoded by the polynucleotide or cDNA thereof.

The present invention also provides a kit for cardiovascular disease diagnosis including the microarray.

The present invention also provides a method of diagnosing cardiovascular disease using the multi-SNP marker.

According to an aspect of the present invention, there is provided a set of polynucleotides for determining by hybridization the genotype pattern at a multi-SNP marker for cardiovascular disease diagnosis. Each polynucleotide in the set comprises (a) a nucleic acid sequence comprising at least 10 contiguous bases of a nucleotide sequence selected from the group consisting of nucleotide sequences SEQ ID NOS: 1 to 35 and wherein the at least 10 contiguous bases comprises a base at a single nucleotide polymorphism (SNP) position in the selected nucleotide sequence, wherein the SNPs are positioned at the 76th nucleotide in SEQ ID NO: 4, at the 85th nucleotide in SEQ ID NO: 8, at the 51st nucleotide in SEQ ID NO: 9, at the 35th nucleotide in SEQ ID NO: 10, at the 85th nucleotide in SEQ ID NO: 19 and at the 101st nucleotide in SEQ ID NOS: 1 to 3, 5 to 7, 11 to 18 and 20 to 35; or (b) the complement of the nucleic acid sequence (a).

The present invention provides a polynucleotide for a SNP for cardiovascular disease diagnosis comprising (a) a nucleic acid sequence comprising at least 10 contiguous bases of a nucleotide sequence selected from the group consisting of nucleotide sequences SEQ ID NOS: 1 to 35 and wherein the at least 10 contiguous bases comprises a base at a single nucleotide polymorphism (SNP) position in the selected nucleotide sequence, wherein the SNPs are positioned at the 76th nucleotide in SEQ ID NO: 4, at the 85th nucleotide in SEQ ID NO: 8, at the 51st nucleotide in SEQ ID NO: 9, at the 35th nucleotide in SEQ ID NO: 10, at the 85th nucleotide in SEQ ID NO: 19 and at the 101st nucleotide in SEQ ID NOS: 1 to 3, 5 to 7, 11 to 18 and 20 to 35; and (b) the complement of the nucleic acid sequence (a).

According to another aspect of the present invention, there is provided a polynucleotide hybridized with the polynucleotide and complementary polynucleotides of the nucleotide sequences.

According to another aspect of the present invention, there is provided a microarray for cardiovascular disease diagnosis including the polynucleotide, the complementary polynucleotides of the nucleotide sequences, the polynucleotide hybridized with one of the polynucleotides, polypeptide encoded by one of the polynucleotides or cDNA thereof.

According to another aspect of the present invention, there is provided a kit for cardiovascular disease diagnosis including the microarray.

According to another aspect of the present invention, there is provided a method for diagnosing cardiovascular disease including determining for a subject a genotype of a single nucleotide polymorphism (SNP), wherein the SNP is one of the SNPs comprising a multi-SNP marker selected from multi-SNP marker numbers 1-12 in Table 2, wherein the SNP is identified by a polynucleotide selected from the group consisting of nucleotide sequences of SEQ ID NOS: 1 to 35, and wherein the SNP is positioned in the selected sequence at the 76th nucleotide in SEQ ID NO: 4, at the 85th nucleotide in SEQ ID NO: 8, at the 51st nucleotide in SEQ ID NO: 9, at the 35th nucleotide in SEQ ID NO: 10, at the 85th nucleotide in SEQ ID NO: 19 or at the 101st nucleotide in SEQ ID NOS: 1 to 3, 5 to 7, 11 to 18 and 20 to 35.

The above aspects and advantages of the present invention will become more apparent by describing in detail exemplary embodiments thereof.

DETAILED DESCRIPTION OF THE INVENTION

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

A multi-SNP marker for cardiovascular disease diagnosis according to an aspect of the present invention comprises one or more of the SNPS tabulated in Table 1. A SNP can be identified in a nucleic acid by a reference polynucleotide selected from the group consisting of nucleotide sequences SEQ ID NOS: 1 to 35 in Table 1, wherein the SNP is positioned at the $76^{th}$ nucleotide in SEQ ID NO: 4, at the 85th nucleotide in SEQ ID NO: 8, at the $51^{st}$ nucleotide in SEQ ID NO: 9, at the $35^{th}$ nucleotide in SEQ ID NO: 10, at the $85^{th}$ nucleotide in SEQ ID NO: 19 or $101^{st}$ nucleotide in SEQ ID NOS: 1 to 3, 5 to 7, 11 to 18 and 20 to 35.

The SNP Accession No. of a SNP in the National Center for Biotechnology Information (NCBI) dbSNP database indicates a flanking or reference sequence and a position of the SNP within that reference sequence. Those skilled in the art may easily identify the reference sequence and the position of the SNP using the dbSNP rs Accession No. The specific reference sequences corresponding to the rs No. of the SNP registered in NCBI dbSNP may change over time. It is obvious to those skilled in the art that the reference sequences are within the scope of the present invention, even if the corresponding rs number changes.

The column in Table 1 labeled "Polynucleotide containing SNP" provides the sequence identification number for a reference nucleotide sequence for identification of the SNP in a nucleic acid. These nucleotide sequences, SEQ ID NOS: 1 to 35, are each a polymorphic sequence including a polymorphic site. A "polymorphic sequence" is a polynucleotide sequence including a polymorphic site at which a SNP occurs. All or only part of the polymorphic sequence flanking the polymorphic site can be used by the skilled practitioner to identify the SNP in a nucleic acid.

The nucleotide sequences of SEQ ID NOS: 1 to 35 are also polynucleotides including the base sequences of SNPs. The polynucleotide sequences can be DNA or RNA.

Some characteristics of the SNPs are disclosed in Table 1.

TABLE 1

| SNP Accession No. in NCBI dbSNP | Polynucleotide containing SNP | Involved No. in multi-SNP marker | Band | Gene | SNP function |
|---|---|---|---|---|---|
| rs4459610 | SEQ ID NO: 1 | 1 | 17q23.3 | ACE | Coding exon |
| rs20568 | SEQ ID NO: 2 | 1 | 3q13.33 | ADPRH | Coding exon |
| rs5050 | SEQ ID NO: 3 | 1 | 1q42.2 | AGT | Promoter |
| rs1404396 | SEQ ID NO: 4 | 1 | 7p21.1 | ANKMY2 | Intron |
| rs511678 | SEQ ID NO: 5 | 1 | 1q32.2 | CR2 | Intron |
| rs1916382 | SEQ ID NO: 6 | 1 | 10q21.3 | CTNNA3 | Intron |
| rs995717 | SEQ ID NO: 7 | 1 | 21q22.13 | DSCR4 | Intron |
| rs2611 | SEQ ID NO: 8 | 1 | 10q22.1 | FLJ22761 | Exon |
| rs1805564 | SEQ ID NO: 9 | 1 | 3q26.33 | FXR1 | Intron |
| rs1469876 | SEQ ID NO: 10 | 1 | 1p31.3 | KIAA1573 | Intron |
| rs251692 | SEQ ID NO: 11 | 1 | 19q13.32 | LIG1 | Exon |
| rs1409765 | SEQ ID NO: 12 | 1 | 1p31.1 | LPHN2 | Intron (boundary) |
| rs889179 | SEQ ID NO: 13 | 1 | 19p13.2 | MGC15716 | 3' UTR |
| rs882432 | SEQ ID NO: 14 | 1 | 22q12.1 | MYO18B | Intron |
| rs1801 | SEQ ID NO: 15 | 1 | 4q24 | NFKB1 | Intron |
| rs973126 | SEQ ID NO: 16 | 1 | 4q25 | PAPSS1 | Coding exon |
| rs361594 | SEQ ID NO: 17 | 1 | 22q11.21 | PEX26 | 3' UTR |
| rs734072 | SEQ ID NO: 18 | 1 | 3p21.31 | SCOTIN | Intron |
| rs731710 | SEQ ID NO: 19 | 1 | 16q24.2 | SLC7A5 | Intron |
| rs991827 | SEQ ID NO: 20 | 1 | 12q24.32 | | |
| rs1566307 | SEQ ID NO: 21 | 1 | 12q24.21 | | |
| rs1467523 | SEQ ID NO: 22 | 1 | 14q22.1 | | |
| rs378660 | SEQ ID NO: 23 | 2 | 16q23.1 | | |
| rs1546642 | SEQ ID NO: 24 | 1 | 2p21 | | |
| rs209176 | SEQ ID NO: 25 | 1 | 6p22.1 | | |
| rs1056409 | SEQ ID NO: 26 | 1 | 9q33.1 | | |
| rs1859754 | SEQ ID NO: 27 | 1 | 7q21.13 | | |
| rs1527509 | SEQ ID NO: 28 | 1 | 21q21.1 | | |
| rs1028140 | SEQ ID NO: 29 | 1 | 2q14.1 | | |
| rs1983628 | SEQ ID NO: 30 | 1 | 20q13.2 | | |
| rs557831 | SEQ ID NO: 31 | 1 | 11q24.2 | | |
| rs1194029 | SEQ ID NO: 32 | 1 | 12q24.32 | | |
| rs388332 | SEQ ID NO: 33 | 1 | 21q22.2 | | |
| rs2055018 | SEQ ID NO: 34 | 1 | 11p14.1 | | |
| rs1557771 | SEQ ID NO: 35 | 1 | 7p21.1 | | |

'Involved No. in multi-SNP marker' in Table 1 indicates how many multi-SNP markers in Table 2 comprise the particular SNP.

'Band' indicates the chromosomal location of the SNP, where 'p' is the short arm of the chromosome from the centromere, 'q' is the long arm from the centromere, and the numbers are the band numbers. For example, when the 'band' of the SNP positioned in SEQ ID NO: 1 is 17q23.3, the SNP is located in the long arm (q) of the $17^{th}$ chromosome and in the band 23.3 region.

'Gene' refers to the gene including the SNP, where known.

'SNP function' indicates a role performed by the SNP within the gene, where known.

One aspect of the invention provides a set of polynucleotides for cardiovascular disease (CVD) diagnosis. The set of polynucleotides can be used to determine the genotype pattern at a multi-SNP marker for CVD diagnosis disclosed herein. Each polynucleotide comprises (a) a nucleic acid sequence comprising at least 10 contiguous bases of a nucleotide sequence selected from the group consisting of nucleotide sequences SEQ ID NOS: 1 to 35 and wherein the at least 10 contiguous bases comprises a base at a single nucleotide polymorphism (SNP) position in the selected nucleotide sequence, wherein the SNPs are positioned at the $76^{th}$ nucleotide in SEQ ID NO: 4, at the $85^{th}$ nucleotide in SEQ ID NO: 8, at the $51^{st}$ nucleotide in SEQ ID NO: 9, at the $35^{th}$ nucleotide in SEQ ID NO: 10, at the $85^{th}$ nucleotide in SEQ ID NO: 19 and at the $101^{st}$ nucleotide in SEQ ID NOS: 1 to 3, 5 to 7, 11 to 18 and 20 to 35; or (b) the complement of the nucleic acid sequence (a).

In one embodiment, the set comprises polynucleotides for determining the genotype of at least two of the SNPs comprising the multi-SNP marker. In another embodiment, the set comprises polynucleotides for determining the genotype of each of the SNPs comprising the multi-SNP market. In yet another embodiment, the set comprises polynucleotides for determining the genotype at each of the SNPs in Table 1.

In an embodiment of the present invention, a genotype in a nucleic acid of a SNP of a multi-SNP marker may be one of the genotypes presented in Table 2, below, for the SNP.

The multi-SNP marker according to the present embodiment may be one of twelve multi-SNP markers which are combinations of the single SNPs listed in Table 1. The combinations of SNPs, as represented by the reference SEQ ID NOS for each SNP in a combination, and the genotypes thereof are disclosed in Table 2. 'Multi-SNP marker' in Table 2 indicates a combination of three selected single SNPs. 'Genotype' represents the genotypes for the single SNPs in the order of SEQ ID NOS of the multi-SNP marker determined by the inventors to be characteristic of the diseased population. For example, for No. 1 of Table 2, the genotypes of 'rs20568' (SEQ ID NO: 2), 'rs209176' (SEQ ID NO: 25) and 'rs5050' (SEQ ID NO: 3) are respectively CC, CC, TG.

In another embodiment of the present invention, cardiovascular disease may be myocardial infarction, angina pectoris, atherosclerosis, hyperpiesia, cardiac failure, aneurysm, arteriosclerosis, embolism, stroke or thrombosis, and is myocardial infarction in one embodiment of the present invention.

In Examples of the present invention, a series of selections were made in order to find a combination of single SNPs, i.e. a multi-SNP marker, which correspond to a high incidence of cardiovascular disease.

The multi-SNP marker selection was performed using male subjects. After DNA as isolated from the blood of male patients having cardiovascular disease and normal males and amplified, a specific SNP combination and the genotype thereof which were particularly shown in the male patients, and not in normal male persons, were identified.

The identified SNP combinations and the genotype thereof are illustrated in Table 2. The statistical characteristics of the multi-SNP markers are described in Table 3 below.

TABLE 3

| No. | Appearance frequency of patient group | Appearance frequency of normal group | Odds ratio | 95% confidence interval | |
|---|---|---|---|---|---|
| 1 | 30 | 0 | 61.3 | 3.7 | 1010 |
| 2 | 30 | 0 | 61.3 | 3.7 | 1010 |

TABLE 2

| Polymorphic Sequences of SNPS No. in Multi-SNP Marker | Genotype correlated with cardiovascular disease |
|---|---|
| 1 (SEQ ID NO: 2, SEQ ID NO: 25, SEQ ID NO: 3) | (CC, CC, TG) |
| 2 (SEQ ID NO: 11, SEQ ID NO: 15, SEQ ID NO: 35) | (CC, GC, TT) |
| 3 (SEQ ID NO: 6, SEQ ID NO: 23, SEQ ID NO: 16) | (CC, AG, TT or TC) |
| 4 (SEQ ID NO: 20, SEQ ID NO: 22, SEQ ID NO: 13) | (AA or AC, CG, TT or TG) |
| 5 (SEQ ID NO: 17, SEQ ID NO: 1, SEQ ID NO: 31) | (TC or CC, TT or TA, TT or TG) |
| 6 (SEQ ID NO: 5, SEQ ID NO: 29, SEQ ID NO: 8) | (GC, TT or TC, GC) |
| 7 (SEQ ID NO: 27, SEQ ID NO: 30, SEQ ID NO: 32) | (CC, CC, AA or AG) |
| 8 (SEQ ID NO: 26, SEQ ID NO: 19, SEQ ID NO: 7) | (TG, TC or CC, GG) |
| 9 (SEQ ID NO: 23, SEQ ID NO: 9, SEQ ID NO: 28) | (AG, GG, TC or CC) |
| 10 (SEQ ID NO: 21, SEQ ID NO: 14, SEQ ID NO: 4) | (CT, AG or GG, CT or TT) |
| 11 (SEQ ID NO: 10, SEQ ID NO: 18, SEQ ID NO: 33) | (TT or TC, CG or GG, AC) |
| 12 (SEQ ID NO: 24, SEQ ID NO: 12, SEQ ID NO: 34) | (AC, CC or CG, TA) |

TABLE 3-continued

| No. | Appearance frequency of patient group | Appearance frequency of normal group | Odds ratio | 95% confidence interval | |
|---|---|---|---|---|---|
| 3  | 28 | 0 | 56.7  | 3.4 | 935.5 |
| 4  | 25 | 0 | 50    | 3   | 826.5 |
| 5  | 25 | 0 | 50    | 3   | 826.5 |
| 6  | 24 | 0 | 47.8  | 2.9 | 790.9 |
| 7  | 23 | 0 | 45.6  | 2.8 | 755.7 |
| 8  | 28 | 1 | 27.7  | 3.7 | 205.7 |
| 9  | 33 | 1 | 33.5  | 4.5 | 247.6 |
| 10 | 35 | 3 | 11.9  | 3.6 | 39.22 |
| 11 | 29 | 2 | 14.4  | 3.4 | 60.98 |
| 12 | 34 | 3 | 11.5  | 3.5 | 37.94 |

'No.' in Table 3 corresponds to the multi-SNP marker No. in Table 2.

'Appearance frequency of patient group' refers to the number of patients having the multi-SNP marker among all 221 inspected patients. 'Appearance frequency of normal group' refers to the number of men with the multi-SNP markers among 192 inspected normal persons.

'Odds ratio' indicates the ratio of the probability of the multi-SNP marker in the patient group to the probability of the multi-SNP marker in the normal group. That is, the odds ratio is ad/bc where a indicates the appearance frequency of the multi-SNP marker in the patient group, c indicates the appearance frequency of the multi-SNP marker in the normal group, b=[(total number of inspected patients)−a] and d=[(total number of normal unaffected men)−c]. The number of inspected patients and normal persons were respectively 221 and 192, and therefore b=[221−a] and d=[192−c].

If the odds ratio exceeds 1, there is an association between the multi-SNP marker and the patient group. The degree of the association increases with the odds ratio. As indicated in Table 3, the multi-SNP marker Nos. 1 through 12 according to an embodiment of the present invention have odds ratios ranging between 11.5 and 61.3. Since the values are much greater than 1, it is estimated that there is a close association between the multi-SNP marker Nos. 1 through 12 according to an embodiment of the present invention and the incidence of cardiovascular disease.

'95% confidence interval' indicates that there is a 95% chance that the interval contains the actual odds ratio, and is obtained using the following formula. When 1 is within the confidence interval, i.e. the lower bound is below 1 and the upper bound is above 1, it is interpreted to mean that there is no association between the multi-SNP marker and the cardiovascular disease.

$$95\% \text{ confidence interval} = (\text{lower bound, upper bound})$$
$$= (\text{odds ratio} \times \exp(-1.960\sqrt{\vec{V}}), \text{odds ratio} \times \exp(1.960\sqrt{\vec{V}})),$$

where $V=1/a+1/b+1/c+1/d$.

The multi-SNP marker for cardiovascular disease diagnosis according to an embodiment of the present invention may include one of the multi-SNP markers, two or more of the multi-SNP markers, for example, all of the multi-SNP markers of Nos. 1 to 12.

The polynucleotides of the single SNPs included in the multi-SNP marker for cardiovascular disease diagnosis may include at least 10 contiguous bases, for example, 10 to 100 contiguous bases.

An allele specific polynucleotide for cardiovascular disease diagnosis according to another aspect of the present invention can be hybridized with the polynucleotide or complementary polynucleotide thereof according to an embodiment of the present invention.

The allele-specific polynucleotide is a polynucleotide specifically hybridized with the allele. The hybridization should be done in order to distinguish the bases of a SNP at the polymorphic sites of SEQ ID NOS: 1 to 35 specifically. The hybridization is performed under a strict condition, for example in a salt concentration of 1 M or less and at a temperature of 25° C. or higher. For example, 5×SSPE (750 mM NaCl, 50 mM Na Phosphate, 5 mM EDTA, pH 7.4) and 25 to 30° C. may be suitable conditions for the allele specific probe hybridization. The hybridization conditions may be changed according to desired use by those skilled in the art.

The allele specific polynucleotide can be a primer. A primer refers to a single-strand oligonucleotide capable of initiating template-directed DNA synthesis in an appropriate buffer under appropriate conditions, for example in the presence of four different nucleotide triphosphates and a polymerizing agent such as DNA, RNA polymerase or reverse transcriptase at a proper temperature. The length of the primer may vary according to the purpose of use, but is usually 15 to 30 nucleotides. A short primer molecule generally requires a lower temperature to be stably hybridized with the template. The primer sequence does not necessarily need to be completely complementary to the template, but should be sufficiently complementary to be hybridized with the template. The primer has a 3' end arranged so as to correspond to the polymorphic sites of SEQ ID NOS: 1 to 35. The primer is hybridized with the target DNA including the polymorphic site and initiates amplification of an allele having complete homology to the primer. The primer and the other primer hybridized at the opposite side are used as a primer pair. Amplification is performed using the two primers, indicating that there is a specific allele. According to an embodiment of the present invention, the primer includes a polynucleotide fragment used in a ligase chain reaction (LCR).

In an embodiment of the present invention, an allele specific polynucleotide may be a probe. The probe is a hybridization probe, which is an oligonucleotide capable of binding specifically to a complementary strand of a nucleic acid. Such a probe includes a peptide nucleic acid introduced by Nielsen et al., Science 254, 1497-1500 (1991). According to an embodiment of the present invention, the probe is an allele specific probe. When a polymorphic site is located in nucleic acid fragments derived from two members of the same species, the allele specific probe is hybridized with the DNA fragment derived from one member but is not hybridized with the DNA fragment derived from the other member. In this case, the hybridization conditions can be sufficiently strict for hybridization with only one allele by showing a significant difference between intensities of hybridization for different alleles. According to an embodiment of the present invention, the probe is arranged such that its central site is the polymorphic site of the sequence, for example the $7^{th}$ position in a probe consisting of 15 nucleotides, or the $8^{th}$ or $9^{th}$ position in a probe consisting of 16 nucleotides. In this way, a hybridization difference for different alleles can be obtained. According to an embodiment of the present invention, the probe can be used in a diagnosis method for detecting an allele, etc. The diagnosis method may be Southern blotting in which detection is performed using the hybridization of nucleic acids of a method in which a microarray to which the probe was bound in advance is used.

A microarray for cardiovascular disease diagnosis according to another aspect of the present invention includes the polynucleotide or the complementary nucleotide thereof, the polynucleotide hybridized with one of the polynucleotides, a polypeptide encoded by one of the polynucleotides or cDNA thereof according to an embodiment of the present invention.

According to an embodiment of the present invention, the microarray may be prepared using a conventional method known to those skilled in the art using the polynucleotide or the complementary polynucleotide thereof, the polynucleotide hybridized with the probe, the polypeptide encoded by one of the polynucleotides or cDNA thereof according to an embodiment of the present invention.

For example, the polynucleotide may be fixed to a substrate coated with an active group of amino-silane, poly-L-lysine and aldehyde. Also, the substrate may be composed of a silicon wafer, glass, quartz, metal or plastic. The method of fixing the polynucleotide to the substrate may be either micropipetting using piezoelectric or a method using a pin-shaped spotter.

A kit for cardiovascular disease diagnosis according to an aspect of the present invention includes the microarray.

The kit may further include a primer set for isolating and amplifying DNA including the SNPs from the subjects. The appropriate primer set may be easily designed by those skilled in the art with reference to the sequences according to an embodiment of the present invention. For example, the primer set in Table 4 may be used.

A method of diagnosing cardiovascular disease according to another aspect of the present invention uses the multi-SNP markers of the present invention.

The diagnosing method includes determining a genotype of a SNP for a subject, wherein the SNP is one of the SNPS comprising a multi-SNP marker in Table 2. The SNP can be identified by a polynucleotide of SEQ ID NOS: 1 to 35, wherein the SNP is positioned in the reference polynucleotide at the $76^{th}$ nucleotide in SEQ ID NO: 4, at the $85^{th}$ nucleotide in SEQ ID NO: 8, at the $51^{st}$ nucleotide in SEQ ID NO: 9, at the $35^{th}$ nucleotide in SEQ ID NO: 10, at the $85^{th}$ nucleotide in SEQ ID NO: 19 or at the $101^{st}$ nucleotide in SEQ ID NOS: 1 to 3, 5 to 7, 11 to 18 and 20 to 35. The method can further comprise determining the genotype for each SNP in the multi-SNP marker or for each SNP in each multi-SNP marker. The method can also comprise obtaining a sample from the subject, wherein the sample comprises a polypeptide or nucleic acid; or isolating a nucleic acid from the subject.

The DNA isolating may be carried out using a method known to those skilled in the art. For example, DNA can be directly purified from tissues or cells or a specific region can be amplified using a Polymerase Chain Reaction (PCR), etc. and isolated. In the description, DNA refers to not only DNA, but also cDNA synthesized from mRNA. Obtaining nucleic acids from a subject may be carried out by one of PCR amplification, ligase chain reaction (LCR) (Wu and Wallace, *Genomics* 4, 560(1989), Landegren etc., *Science* 241, 1077 (1988)), transcription amplification (Kwoh etc., *Proc. Natl. Acad. Sci. USA* 86, 1173(1989)), self-sustained sequence replication (Guatelli etc., *Proc. Natl. Acad. Sci. USA* 87, 1874 (1990)) and Nucleic Acid Sequence Based Amplification (NASBA).

Sequencing the isolated DNA may be performed through various methods known to those skilled in the art. For example, the nucleotides of nucleic acids may be directly sequenced using a dideoxy method. Also, the nucleotides of the polymorphic sites may be sequenced by hybridizing the DNA with a probe containing the sequence of the SNP site or a complementary probe thereof, and examining the degree of the hybridization. The degree of hybridization may be measured using a method of indicating a detectable index of the target DNA and specifically detecting the hybridized target, or using an electrical signal detecting method. The determining of the genotype of a polymorphic site may include hybridizing the nucleic acid sample isolated from the subject with the polynucleotide including the SNP according to an embodiment of the present invention and a polynucleotide hybridized with the polynucleotide, and detecting the results of the hybridization. Additionally, determining the genotype of a SNP may be performed using the mass spectrometry method of the Examples, or any other suitable methods known in the art.

The method of diagnosing cardiovascular disease can further include judging that the subject belongs to the high risk group having a high incidence or probability of cardiovascular disease when the genotype for the SNP matches the genotype associated with cardiovascular disease listed in Table 2 for that SNP in the selected multi-SNP marker. Additionally, the method may comprise determining the genotype of each SNP in the selected multi-SNP marker for the subject and judging that the subject has an increased risk of incidence of cardiovascular disease when the determined genotype for each SNP in the selected multi-SNP marker matches the genotype associated with cardiovascular disease listed in Table 2 for that SNP.

The present invention will now be described in greater detail with reference to the following examples. The following examples are for illustrative purposes only and are not intended to limit the scope of the invention.

Example 1

Multi-SNP Marker Selection

DNA samples were isolated from blood of a patient group diagnosed with and treated for a cardiovascular disease and from a normal group without symptoms of cardiovascular disease. The appearance frequency of the alleles of a specific SNP was then analyzed. The patient group and the normal group both consisted of Koreans. The SNPs of the Example were selected from a published database, either NCBI dbSNP (Single Nucleotide Polymorphism Database) or SEQUENOM RealSNP™ Assay Database. The SNPs were analyzed using a primer which hybridized close to the selected SNPs.

1-1. Preparation of DNA Sample

DNA was extracted from blood of a patient group consisting of 221 Korean male patients diagnosed with and treated for cardiovascular disease. DNA was also extracted from a normal group consisting of 192 Korean men not having myocardial infarction symptoms. Chromosomal DNA extraction was carried out using a known extraction method (A Laboratory Manual, p 392, Sambrook, Fritsch and Maniatis, 2nd edition, Cold Spring Harbor Press, 1989) and instructions for a commercially available kit (Gentra system, D-50K). Only DNA having a purity of at least 1.7, measured using UV (260/280 nm), was selected from the extracted DNA and used.

1-2. Amplification of the Target DNA

The target DNA having a certain DNA region including at least one of the 705 SNPs to be analyzed was amplified using a PCR. The PCR was performed using a conventional method and the conditions were as indicated below. First, the chromosomal DNA was diluted to a concentration of 2.5 ng/ml. Then the following PCR mixture was prepared.

| | |
|---|---|
| Water (HPLC grade) | 2.24 µl |
| 10 × buffer (containing 15 mM MgCl₂, 25 mM MgCl₂) | 0.5 µl |
| dNTP mix (GIBCO) (25 mM/each) | 0.04 µl |
| Taq pol (HotStart) (5 U/µl) | 0.02 µl |
| Forward/reverse primer mix (1 µM/each) | 0.02 µl |
| DNA | 1.00 µl |
| Total volume | 5.00 µl |

The forward and reverse primers were selected upstream and downstream from the SNPs at proper positions in a known reference sequence to yield target DNA fragments containing 200 nucleotides or less from the amplification reactions. Several of the 705 sets of primers are indicated in Table 4.

Thermal cycling of PCR was performed by maintaining the temperature at 95° C. for 15 minutes, cycling the temperature from 95° C. for 30 seconds, to 56° C. for 30 seconds to 72° C. for 1 minute a total of 45 times, maintaining the temperature at 72° C. for 3 minutes, and then storing at 4° C.

1-3. Analysis of SNP of the Amplified Target DNA

SNP analysis of the target DNA fragments was performed using a homogeneous Mass Extend (hME) technique from Sequenom. The principle of the hME technique is as follows. First, a primer, also called an extension primer, complementary to bases up to just before the SNP of the target DNA fragment was prepared. The primer was hybridized with the target DNA fragment and DNA polymerization was facilitated. At this time, added to the reaction solution was a reagent (Termination mix, e.g. ddTTP) for terminating the polymerization after the base complementary was added to a first allele base (e.g. 'A' allele) among the subject SNP alleles. As a result, when the target fragment DNA included the first allele (e.g. 'A' allele), a product containing only one base complementary to the first allele (e.g. 'T') added was obtained. On the other hand, when the target DNA fragment included a second allele (e.g. 'G' allele), a product having a base complementary to the second allele (e.g. 'C') extending to the first allele base (e.g. 'A') was obtained. The length of the product extending from the primer was determined using mass analysis to determine the type of allele in the target DNA. Specific experimental conditions were as follows.

First, free dNTPs were removed from the PCR product. To this end, 1.53 µl of pure water, 0.17 µl of an hME buffer, and 0.30 µl of shrimp alkaline phosphatase (SAP) were added to a 1.5 ml tube and mixed to prepare SAP enzyme solution. The tube was centrifuged at 5,000 rpm for 10 seconds. Then, the PCR product was put into the SAP solution tube, sealed, maintained at 37° C. for 20 minutes and at 85° C. for 5 minutes and then stored at 4° C.

Next, a homogeneous extension was performed using the target DNA product as a template. The reaction solution was as follows.

| | |
|---|---|
| Water (nanopure grade) | 1.728 µl |
| hME extension mix (10 × buffer containing 2.25 mM d/ddNTPs) | 0.200 µl |
| Extension primer (each 100 µM) | 0.054 µl |
| Thermosequenase (32 U/µl) | 0.018 µl |
| Total volume | 2.00 µl |

The reaction solution was mixed well and spin down centrifuged. A tube or plate containing the reaction solution was sealed and maintained at 94° C. for 2 minutes, cycled from 94° C. for 5 seconds, to 52° C. for 5 seconds to 72° C. for 5 seconds a total of 40 times, and then stored at 4° C. The obtained homogeneous extension product was washed with a resin (SpectroCLEAN, Sequenom, #10053) and a salt was removed. Several of the 705 extension primers used for homogeneous extension are disclosed in Table 4.

TABLE 4

| SEQ ID NO: containing SNP | Primer for target DNA amplification (SEQ ID NO:) | | Extension primer (SEQ ID NO:) |
|---|---|---|---|
| | Forward primer | Reverse primer | |
| 1 | 36 | 37 | 38 |
| 2 | 39 | 40 | 41 |
| 3 | 42 | 43 | 44 |
| 4 | 45 | 46 | 47 |
| 5 | 48 | 49 | 50 |
| 6 | 51 | 52 | 53 |
| 7 | 54 | 55 | 56 |
| 8 | 57 | 58 | 59 |
| 9 | 60 | 61 | 62 |
| 10 | 63 | 64 | 65 |
| 11 | 66 | 67 | 68 |
| 12 | 69 | 70 | 71 |
| 13 | 72 | 73 | 74 |
| 14 | 75 | 76 | 77 |
| 15 | 78 | 79 | 80 |
| 16 | 81 | 82 | 83 |
| 17 | 84 | 85 | 86 |
| 18 | 87 | 88 | 89 |
| 19 | 90 | 91 | 92 |
| 20 | 93 | 94 | 95 |
| 21 | 96 | 97 | 98 |
| 22 | 99 | 100 | 101 |
| 23 | 102 | 103 | 104 |
| 24 | 105 | 106 | 107 |
| 25 | 108 | 109 | 110 |
| 26 | 111 | 112 | 113 |
| 27 | 114 | 115 | 116 |
| 28 | 117 | 118 | 119 |
| 29 | 120 | 121 | 122 |
| 30 | 123 | 124 | 125 |
| 31 | 126 | 127 | 128 |
| 32 | 129 | 130 | 131 |
| 33 | 132 | 133 | 134 |
| 34 | 135 | 136 | 137 |
| 35 | 138 | 139 | 140 |

Mass analysis was performed on the obtained extension product to determine the sequence of a polymorphic site using Matrix Assisted Laser Desorption and Ionixation-Time of Flight (MALDI-TOF). In the MALDI-TOF, a material to be analyzed was exposed to a laser beam and flew with an ionized matrix (3-Hydroxypicolinic acid) in a vacuum to a detector. The flight time to the detector was calculated to determine the mass. A light material can reach the detector in a shorter amount of time than a heavy material. The nucleotide sequences of SNPs in the target DNA may be determined based on differences in mass and known nucleotide sequences of the SNPs.

The possible alleles of each SNP found to have diagnostic value are presented in the nucleotide sequences shown in Table 1. Each allele may exist in the form of a homozygote or a heterozygote in a subject. According to Mendel's Law of inheritance and the Hardy-Weinberg Law, the genetic makeup of alleles constituting a population is maintained at a constant frequency. When the allelic frequencies for a given SNP differ in the diseased vs normal group (i.e., in the diseased group vs the allelic frequency predicted via Hardy-Weinberg equilibrium for the general population as represented by the normal group) at a statistically significant level, the deviation suggests predictive value, and thus, can be efficiently used in the diagnosis of cardiovascular disease. The 705 SNPs according to embodiments of the present invention occur in both populations, since the chosen SNPs are frequent enough to be identified in a general population and deposited in public databases.

1-4. Selection of Multi-SNP Markers

A combination of SNPs, i.e., multi-SNP markers, frequently found in the patients having cardiovascular disease was selected based on the analyzed 705 SNP sequences of 221 male patients having cardiovascular disease and 192 normal men.

First, it was determined that there are about $7.3 \times 10^9$ possible multi-SNP markers composed of one to three of the 705 SNPs.

After the first screening, 11,582,361 multi-SNP markers having a genotype ratio of 2 or higher and a genotype difference of 0.1×(total number of patients, i.e. 221) or higher were selected.

Genotype ratio=(number of patients having a certain genotype)/(number of normal persons having the genotype)

Genotype difference=(number of patients having a certain genotype)−(number of normal persons having the genotype)

Further, 5,348 multi-SNP markers having a p-value of $10^{-6}$ or less for the difference of the frequency of the genotype pattern in the diseased and normal groups were selected. The p-value obtained using Fisher's exact test is a variable used for examining more precise statistical significance. According to an embodiment of the present invention, when the p-value is $10^{-6}$ or less, the genotype indicates a risk factor or a protective factor, thereby proving a significant relationship between the genotype and the disease.

In a second screening, odds ratio, 95% confidence interval and 99% confidence interval of the odds ratio were used. The odds ratio is defined as ad/bc, where a, b, c and d are defined in Table 5. If the odds ratio exceeds 1, it indicates that the genotype operates as a risk factor of cardiovascular disease.

TABLE 5

|  | Number of persons containing a certain multi-SNP marker genotype | Number of persons not containing a certain multi-SNP marker genotype |
| --- | --- | --- |
| Patent group frequency | A | b |
| Normal group frequency | C | d |

The 95% confidence interval of the odds ratio=(odds ratio× $\exp(-1.960\sqrt{\vec{V}})$, odds ratio× $\exp(1.960\sqrt{\vec{V}}))$ and the 99% confidence interval of the odds ratio=(odds ratio× $\exp(-2.576\sqrt{\vec{V}})$, odds ratio× $\exp(2.576\sqrt{\vec{V}}))$, where V=1/a+1/b+1/c+1/d Among the selected 5,348 multi-SNP markers, 2,826 multi-SNP markers were selected by selecting the multi-SNP markers having 2.0 or higher as lower bound of the 95% confidence interval, selecting the multi-SNP marker having an odds ratio of 3.0 or higher, and then selecting the multi-SNP markers having 2.0 or higher as lower bound of 99% confidence interval. When the odds ratio and the lower bounds of the 95% and 99% confidence intervals exceed 1.0, the results are statistically significant. However, the required standards were set to 2.0, 3.0 and 2.0 respectively in order to select the most effective markers.

Among the 2,826 multi-SNP markers, twelve multi-SNP markers, which are composed of small numbers of single SNPs and which had a high odds ratio, that is, high coverage for the patient group and low coverage for the normal group, were selected using a Greedy method (Cormen et al., "Introduction to Algorithms", MIT Press, 2001) which is an optimizing method. The twelve multi-SNP markers are disclosed in Table 2.

Example 2

Preparation of SNP Immobilized Microarray

A microarray was prepared by immobilizing polynucleotides to genotype the selected SNPs on a substrate. That is, polynucleotides including 20 contiguous nucleotides of SEQ ID NOS:1-35, wherein each polynucleotide contained a base of an SNP located in the $11^{th}$ of 20 contiguous nucleotides of the nucleotide sequences in Table 1 were immobilized on the substrate. In SEQ ID NOS:1-35, the SNPs are positioned at the $76^{th}$ nucleotide in SEQ ID NO: 4, at the $85^{th}$ nucleotide in SEQ ID NO: 8, at the $51^{st}$ nucleotide in SEQ ID NO: 9, at the $35^{th}$ nucleotide in SEQ ID NO: 10, at the $85^{th}$ nucleotide in SEQ ID NO: 19 or at the $101^{st}$ nucleotide in SEQ ID NOS: 1 to 3, 5 to 7, 11 to 18 and 20 to 35. Two polynucleotides per each SNP sequence were immobilized on the substrate, one for each of the two alleles of each SNP.

First, the 5'-ends of each of the polynucleotides were substituted with an amine group and the polynucleotides were spotted onto a silylated slide (Telechem) where 2×SSC (pH 7.0), a spotting buffer, was used. After the spotting, binding was induced by increasing the temperature of the slide to 95° C. for 2 minutes in a drying machine. Free polynucleotides were removed by washing with a blocking solution (1.0 g $NaBH_4$, PBS(pH 7.4) 300 mL, EtOH 100 mL) for 15 minutes, a 0.2% SDS solution for 1 minute and triple distilled water for 2 minutes, and then drying at room temperature.

Example 3

Diagnosis of Cardiovascular Disease Using the Microarray

Target DNA was isolated from the blood of the subject to diagnose the incidence or possibility of cardiovascular disease and labeled with a fluorescent material using the method described in Examples 1-1 and 1-2. The fluorescent labeled target DNA was hybridized with the microarray prepared in Example 2 at 42° C. for 4 hours in UniHyb hybridization solution (TeleChem). The slide was washed twice with 2×SSC at room temperature for 5 minutes and dried in air. The dried slide was scanned using a ScanArray 5000 (GSI Lumonics). The scanned results were anylzed using a QuantArray (GSI Lumonics) and ImaGene software (BioDlscover). The probability of incidence of cardiovascular disease and the susceptibility thereto were measured by identifying whether the subject had a partial or whole multi-SNP marker according to an embodiment of the present invention.

The SNPs according to the present invention can be used for the diagnosis and treatment of cardiovascular disease. By using the microarray and the kit including the SNPs of the present invention, cardiovascular disease can be effectively diagnosed. According to the analysis of SNPs related to cardiovascular disease of the present invention, the presence or the risk of cardiovascular disease can be effectively diagnosed.

While the present invention has been particularly shown and described with reference to exemplary embodiments thereof, it will be understood by those of ordinary skilled in the art that various changes in form and details may be made therein without departing from the spirit and scope of the present invention as defined by the following claims. Any combination of the above-described elements in all possible variations thereof is encompassed by the invention unless otherwise indicated herein or otherwise clearly contradicted by context.

---

What is claimed is:

1. A microarray consisting of a set of polynucleotides and optionally, a substrate on which the set of polynucleotides is immobilized, the set of polynucleotides consisting of
  (a) at least one isolated polynucleotide selected from
    (i) a polynucleotide consisting of 15 to 100 contiguous bases of SEQ ID NO: 2 wherein the 15 to 100 contiguous bases comprises C at the $101^{st}$ position in SEQ ID NO: 2,
    (ii) a polynucleotide consisting of the complement of the polynucleotide of (i);
    (iii) a polynucleotide consisting of 15 to 100 contiguous bases of SEQ ID NO: 2 wherein the 15 to 100 contiguous bases comprises T at the $101^{st}$ position in SEQ ID NO: 2, and
    (iv) a polynucleotide consisting of the complement of the polynucleotide of (iii);
  (b) at least one isolated polynucleotide selected from
    (v) a polynucleotide consisting of 15 to 100 contiguous bases of SEQ ID NO: 3 wherein the 15 to 100 contiguous bases comprises G at the $101^{st}$ position in SEQ ID NO: 3,
    (vi) a polynucleotide consisting of the complement of the polynucleotide of (v),
    (vii) a polynucleotide consisting of 15 to 100 contiguous bases of SEQ ID NO: 3 wherein the 15 to 100 contiguous bases comprises T at the $101^{st}$ position in SEQ ID NO: 3, and
    (viii) a polynucleotide consisting of the complement of the polynucleotide of (vii);
  (c) at least one isolated polynucleotide selected from
    (ix) a polynucleotide consisting of 15 to 100 contiguous bases of SEQ ID NO: 25, wherein the 15 to 100 contiguous bases comprises C at the $101^{st}$ position in SEQ ID NO: 25,
    (x) a polynucleotide consisting of the complement of the polynucleotide of (ix),
    (xi) a polynucleotide consisting of 15 to 100 contiguous bases of SEQ ID NO: 25, wherein the 15 to 100 contiguous bases comprises T at the $101^{st}$ position in SEQ ID NO: 25, and
    (xii) a polynucleotide consisting of the complement of the polynucleotide of (xi); and optionally
  (d) at least one isolated polynucleotide consisting of 15 to 100 contiguous bases of a sequence selected from
    (xiii) SEQ ID NOS: 1, 4-24, and 26-35, wherein the 15 to 100 contiguous bases comprises a base at a single nucleotide polymorphism (SNP) position in the selected sequence, wherein the SNP is positioned at the $76^{th}$ nucleotide in SEQ ID NO: 4, the $85^{th}$ nucleotide in SEQ ID NO: 8, the $51^{St}$ nucleotide in SEQ ID NO: 9, the $35^{th}$ nucleotide in SEQ ID NO: 10, the $85^{th}$ nucleotide in SEQ ID NO: 19 or the $101^{st}$ nucleotide in SEQ ID NOS: 1, 5-7, 11-18, 20-24, and 26-35; or
    (xiv) a polynucleotide consisting of the complement of the polynucleotide of (xiii).

2. The microarray of claim 1, wherein the polynucleotides are immobilized on a substrate coated with an active group selected from the group consisting of amino-silane, poly-L-lysine and aldehyde.

3. The microarray of claim 2, wherein the substrate is composed of a material selected from the group consisting of silicon, glass, quartz, metal and plastic.

4. A kit comprising a microarray consisting of a substrate and a set of polynucleotides immobilized on the substrate, the set of polynucleotides consisting of
  (a) at least one isolated polynucleotide selected from
    (i) a polynucleotide consisting of 15 to 100 contiguous bases of SEQ ID NO: 2 wherein the 15 to 100 contiguous bases comprises C at the $101^{st}$ position in SEQ ID NO: 2,
    (ii) a polynucleotide consisting of the complement of the polynucleotide of (i);
    (iii) a polynucleotide consisting of 15 to 100 contiguous bases of SEQ ID NO: 2 wherein the 15 to 100 contiguous bases comprises T at the $101^{st}$ position in SEQ ID NO: 2, and
    (iv) a polynucleotide consisting of the complement of the polynucleotide of (iii);
  (b) at least one isolated polynucleotide selected from
    (v) a polynucleotide consisting of 15 to 100 contiguous bases of SEQ ID NO: 3 wherein the 15 to 100 contiguous bases comprises G at the $101^{st}$ position in SEQ ID NO: 3,
    (vi) a polynucleotide consisting of the complement of the polynucleotide of (v),
    (vii) a polynucleotide consisting of 15 to 100 contiguous bases of SEQ ID NO: 3 wherein the 15 to 100 contiguous bases comprises T at the $101^{st}$ position in SEQ ID NO: 3, and
    (viii) a polynucleotide consisting of the complement of the polynucleotide of (vii);
  (c) at least one isolated polynucleotide selected from
    (ix) a polynucleotide consisting of 15 to 100 contiguous bases of SEQ ID NO: 25, wherein the 15 to 100 contiguous bases comprises C at the $101^{st}$ position in SEQ ID NO: 25,
    (x) a polynucleotide consisting of the complement of the polynucleotide of (ix),
    (xi) a polynucleotide consisting of 15 to 100 contiguous bases of SEQ ID NO: 25, wherein the 15 to 100 contiguous bases comprises T at the $101^{st}$ position in SEQ ID NO: 25, and
    (xii) a polynucleotide consisting of the complement of the polynucleotide of (xi); and optionally (d) at least one isolated polynucleotide consisting of 15 to 100 contiguous bases of a sequence selected from
  (xiii) SEQ ID NOS: 1, 4-24, and 26-35, wherein the 15 to 100 contiguous bases comprises a base at a single nucleotide polymorphism (SNP) position in the selected sequence, wherein the SNP is positioned at the $76^{th}$ nucleotide in SEQ ID NO: 4, the $85^{th}$ nucleotide in SEQ ID NO: 8, the $51^{St}$ nucleotide in SEQ ID NO: 9, the $35^{th}$ nucleotide in SEQ ID NO: 10, the $85^{th}$ nucleotide in SEQ ID NO: 19 or the $101^{st}$ nucleotide in SEQ ID NOS: 1, 5-7, 11-18, 20-24, and 26-35; or
  (xiv) a polynucleotide consisting of the complement of the polynucleotide of (xiii).

5. A set of polynucleotides, wherein the set consists of
(a) at least one isolated polynucleotide selected from
  (i) a polynucleotide consisting of 15 to 100 contiguous bases of SEQ ID NO: 2 wherein the 15 to 100 contiguous bases comprises C at the $101^{st}$ position in SEQ ID NO: 2,
  (ii) a polynucleotide consisting of the complement of the polynucleotide of (i);
  (iii) a polynucleotide consisting of 15 to 100 contiguous bases of SEQ ID NO: 2 wherein the 15 to 100 contiguous bases comprises T at the $101^{st}$ position in SEQ ID NO: 2, and
  (iv) a polynucleotide consisting of the complement of the polynucleotide of (iii);
(b) at least one isolated polynucleotide selected from
  (v) a polynucleotide consisting of 15 to 100 contiguous bases of SEQ ID NO: 3 wherein the 15 to 100 contiguous bases comprises G at the $101^{st}$ position in SEQ ID NO: 3,
  (vi) a polynucleotide consisting of the complement of the polynucleotide of (v),
  (vii) a polynucleotide consisting of 15 to 100 contiguous bases of SEQ ID NO: 3 wherein the 15 to 100 contiguous bases comprises T at the $101^{st}$ position in SEQ ID NO: 3, and
  (viii) a polynucleotide consisting of the complement of the polynucleotide of (vii);
(c) at least one isolated polynucleotide selected from
  (ix) a polynucleotide consisting of 15 to 100 contiguous bases of SEQ ID NO: 25, wherein the 15 to 100 contiguous bases comprises C at the $101^{st}$ position in SEQ ID NO: 25,
  (x) a polynucleotide consisting of the complement of the polynucleotide of (ix),
  (xi) a polynucleotide consisting of 15 to 100 contiguous bases of SEQ ID NO: 25, wherein the 15 to 100 contiguous bases comprises T at the $101^{st}$ position in SEQ ID NO: 25, and
  (xii) a polynucleotide consisting of the complement of the polynucleotide of (xi); and optionally
(d) at least one isolated polynucleotide consisting of 15 to 100 contiguous bases of a sequence selected from
  (xiii) SEQ ID NOS: 1, 4-24, and 26-35, wherein the 15 to 100 contiguous bases comprises a base at a single nucleotide polymorphism (SNP) position in the selected sequence, wherein the SNP is positioned at the $76^{th}$ nucleotide in SEQ ID NO: 4, the $85^{th}$ nucleotide in SEQ ID NO: 8, the $51^{St}$ nucleotide in SEQ ID NO: 9, the $35^{th}$ nucleotide in SEQ ID NO: 10, the $85^{th}$ nucleotide in SEQ ID NO: 19 or the $101^{st}$ nucleotide in SEQ ID NOS: 1, 5-7, 11-18, 20-24, and 26-35; or
  (xiv) a polynucleotide consisting of the complement of the polynucleotide of (xiii).

6. A method of determining increased risk of cardiovascular disease comprising:
  obtaining a nucleic acid sample from a male human subject;
  hybridizing the nucleic acid sample with the set of polynucleotides of claim 5; and
  detecting the results of the hybridization to determine the genotype of the subject at the single nucleotide polymorphism (SNP) at the $101^{st}$ position in SEQ ID NO: 2 is CC; the genotype of the subject at the SNP at the $101^{st}$ position in SEQ ID NO: 3 is CC; and the genotype of the subject at the SNP at the $101^{st}$ position in SEQ ID NO: 25 is TG; and
  determining that the subject has an increased risk of cardiovascular disease.

\* \* \* \* \*